(12) United States Patent
Ahner et al.

(10) Patent No.: US 9,297,759 B2
(45) Date of Patent: Mar. 29, 2016

(54) CLASSIFICATION OF SURFACE FEATURES USING FLUORESCENCE

(71) Applicant: Seagate Technology LLC, Cupertino, CA (US)

(72) Inventors: Joachim Walter Ahner, Livermore, CA (US); David M. Tung, Livermore, CA (US); Samuel Kah Hean Wong, Johor Bahru (MY); Henry Luis Lott, Fremont, CA (US); Stephen Keith McLaurin, Sunnyvale, CA (US); Maissarath Nassirou, Fremont, CA (US); Florin Zavaliche, San Ramon, CA (US)

(73) Assignee: Seagate Technology LLC, Cupertino, CA (US)

( * ) Notice: Subject to any disclaimer, the term of this patent is extended or adjusted under 35 U.S.C. 154(b) by 105 days.

(21) Appl. No.: 14/032,187

(22) Filed: Sep. 19, 2013

(65) Prior Publication Data

US 2014/0098364 A1    Apr. 10, 2014

Related U.S. Application Data

(60) Provisional application No. 61/710,666, filed on Oct. 5, 2012.

(51) Int. Cl.
*G01N 21/63* (2006.01)
*G01N 21/95* (2006.01)
*G01N 21/47* (2006.01)
(Continued)

(52) U.S. Cl.
CPC ............. *G01N 21/63* (2013.01); *G01N 21/47* (2013.01); *G01N 21/64* (2013.01); *G01N 21/94* (2013.01); *G01N 21/95* (2013.01); *G01N 21/9501* (2013.01)

(58) Field of Classification Search
CPC .......... G01N 15/14; G01N 2015/1472; G01N 2021/8822
USPC ............. 356/237.1–237.6, 450, 239.3, 238.3, 356/239.7
See application file for complete search history.

(56) References Cited

U.S. PATENT DOCUMENTS

| | | |
|---|---|---|
| 4,207,467 A | 6/1980 | Doyle |
| 4,477,890 A | 10/1984 | Ceshkovsky et al. |

(Continued)

FOREIGN PATENT DOCUMENTS

| | | |
|---|---|---|
| JP | 06-241758 A | 9/1994 |
| JP | 08-075661 A | 3/1996 |

(Continued)

OTHER PUBLICATIONS

Candela CS10, Optical X-BeamTM Surface Analyzer, Product Description (www.klatencor.com/defect-inspection/candela-cs10.html), accessed Apr. 17, 2013.

(Continued)

*Primary Examiner* — Kara E Geisel
*Assistant Examiner* — Iyabo S Alli

(57) ABSTRACT

Provided herein is an apparatus, including a photon emitter configured to emit photons onto a surface of an article, a photon detector array configured to receive photons from surface features of the article; and a processing means configured for processing photon-detector-array signals corresponding to photons scattered from the surface features and photons fluoresced from the surface features, wherein the processing means is further configured for classifying the surface features of the article.

19 Claims, 9 Drawing Sheets

Figure 1:
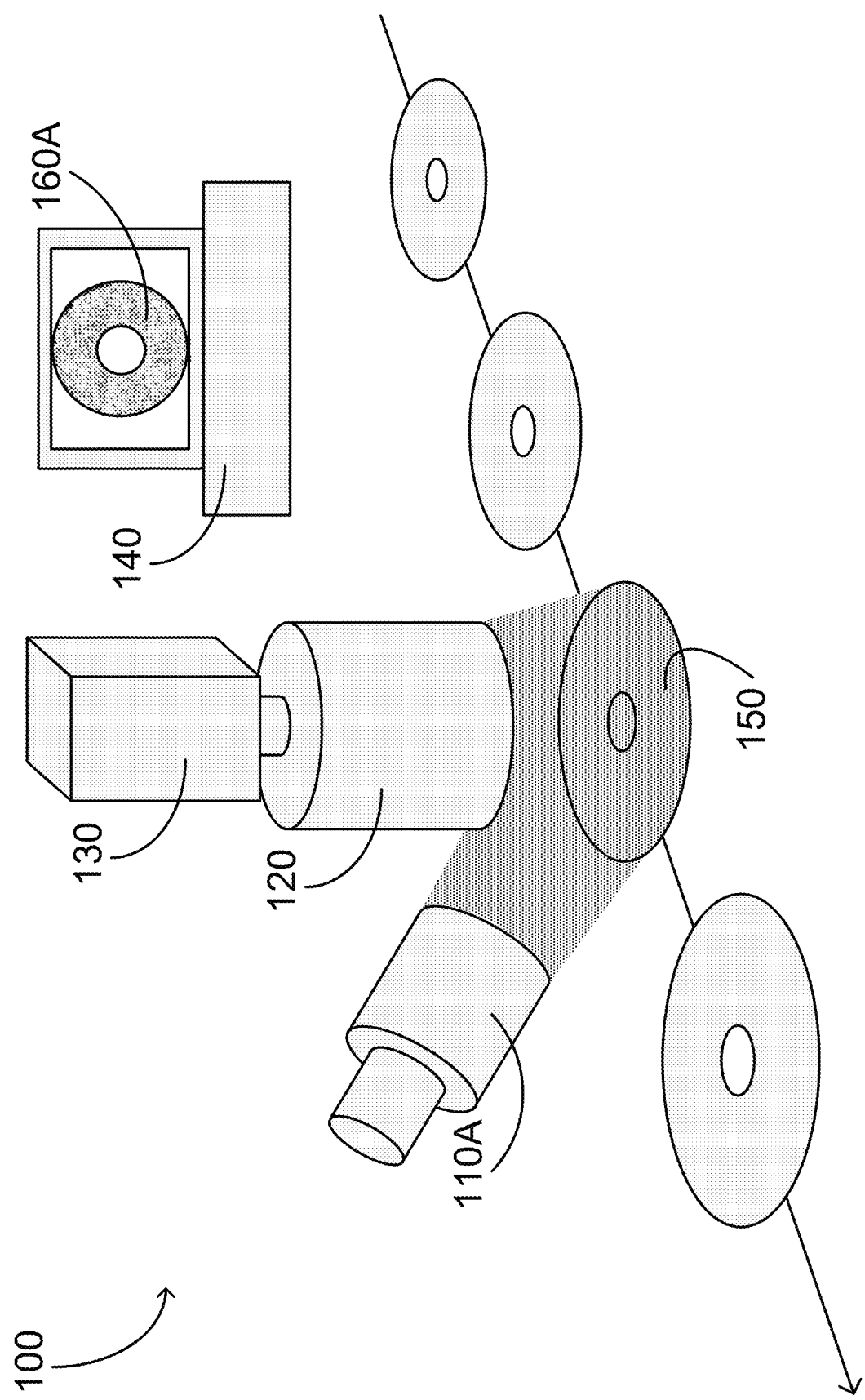

(51) Int. Cl.
*G01N 21/64* (2006.01)
*G01N 21/94* (2006.01)

(56) References Cited

U.S. PATENT DOCUMENTS

| | | | |
|---|---|---|---|
| 4,551,919 A | 11/1985 | Sakata et al. |
| 4,598,997 A | 7/1986 | Auderset et al. |
| 4,618,773 A | 10/1986 | Drukier |
| 4,794,550 A | 12/1988 | Greivenkamp |
| 4,806,776 A | 2/1989 | Kley |
| 4,975,571 A | 12/1990 | McMurtry et al. |
| 5,058,178 A | 10/1991 | Ray |
| 5,066,130 A | 11/1991 | Tsukiji et al. |
| 5,131,755 A | 7/1992 | Chadwick et al. |
| 5,168,322 A | 12/1992 | Clarke et al. |
| 5,455,870 A | 10/1995 | Sepai et al. |
| 5,610,392 A | 3/1997 | Nagayama et al. |
| 5,627,638 A | 5/1997 | Vokhmin |
| 5,661,559 A | 8/1997 | Brezoczky et al. |
| 5,726,455 A | 3/1998 | Vurens |
| 5,737,072 A | 4/1998 | Emery et al. |
| 5,774,212 A | 6/1998 | Corby, Jr. |
| 5,778,039 A | 7/1998 | Hossain et al. |
| 5,781,649 A | 7/1998 | Brezoczky |
| 5,859,698 A | 1/1999 | Chau et al. |
| 5,898,491 A | 4/1999 | Horai et al. |
| 5,933,236 A | 8/1999 | Sommargren |
| 5,973,839 A | 10/1999 | Dorsel |
| 6,256,097 B1 | 7/2001 | Wagner |
| 6,392,745 B1 | 5/2002 | Mavliev et al. |
| 6,449,036 B1 | 9/2002 | Wollmann et al. |
| 6,476,908 B1 | 11/2002 | Watson |
| 6,483,584 B1 | 11/2002 | Lee et al. |
| 6,509,966 B2 | 1/2003 | Ishiguro |
| 6,515,742 B1 | 2/2003 | Ruprecht |
| 6,529,270 B1 | 3/2003 | Bills |
| 6,542,248 B1 | 4/2003 | Schwarz |
| 6,556,783 B1 | 4/2003 | Gelphman |
| 6,559,458 B2 | 5/2003 | Rinn |
| 6,559,926 B2 | 5/2003 | Yamaguchi et al. |
| 6,617,087 B1 | 9/2003 | Rangarajan et al. |
| 6,617,603 B2 | 9/2003 | Ishiguro et al. |
| 6,809,809 B2 * | 10/2004 | Kinney et al. ............... 356/237.5 |
| 6,819,423 B2 | 11/2004 | Stehle et al. |
| 6,822,734 B2 | 11/2004 | Eidelman et al. |
| 6,847,907 B1 | 1/2005 | Novotny |
| 7,207,862 B2 | 4/2007 | Nabeya et al. |
| 7,433,031 B2 | 10/2008 | Xu et al. |
| 7,474,410 B2 | 1/2009 | Moon |
| 7,489,399 B1 | 2/2009 | Lee |
| 7,684,057 B2 | 3/2010 | Sakai |
| 7,751,609 B1 | 7/2010 | Berman |
| 7,777,876 B2 * | 8/2010 | Horai ..................... G01N 21/65 356/237.3 |
| 7,920,254 B2 * | 4/2011 | Mysore ................. G01B 11/26 356/613 |
| 7,969,567 B2 | 6/2011 | Yoshida et al. |
| 8,018,585 B2 | 9/2011 | Hariyama et al. |
| 8,077,305 B2 | 12/2011 | Owen et al. |
| 8,139,232 B2 | 3/2012 | Wolf et al. |
| 8,223,326 B2 | 7/2012 | Kim et al. |
| 8,294,890 B2 | 10/2012 | Usuda |
| 8,547,545 B2 | 10/2013 | Sasazawa et al. |
| 2001/0036588 A1 | 11/2001 | Buschbeck et al. |
| 2002/0088952 A1 | 7/2002 | Rao et al. |
| 2004/0207836 A1 | 10/2004 | Chhibber et al. |
| 2004/0231177 A1 | 11/2004 | Mies |
| 2005/0067740 A1 | 3/2005 | Haubensak |
| 2005/0099204 A1 | 5/2005 | Uh et al. |
| 2005/0174575 A1 | 8/2005 | Norton et al. |
| 2005/0280808 A1 | 12/2005 | Backhauss et al. |
| 2006/0126062 A1 | 6/2006 | Tuschel |
| 2006/0147814 A1 | 7/2006 | Liang |
| 2006/0181700 A1 | 8/2006 | Andrews et al. |
| 2007/0229852 A1 | 10/2007 | Wack et al. |
| 2008/0174771 A1 | 7/2008 | Yan et al. |
| 2008/0191137 A1 | 8/2008 | Poteet et al. |
| 2008/0309927 A1 | 12/2008 | Grueneberg |
| 2009/0009753 A1 | 1/2009 | Horai et al. |
| 2009/0122304 A1 | 5/2009 | Jin et al. |
| 2009/0320051 A1 | 12/2009 | Meerwald et al. |
| 2009/0323051 A1 | 12/2009 | Matsui |
| 2010/0053602 A1 | 3/2010 | Hayashi et al. |
| 2010/0053603 A1 | 3/2010 | Sakaguchi et al. |
| 2010/0091272 A1 | 4/2010 | Asada et al. |
| 2011/0066382 A1 | 3/2011 | Adams |
| 2011/0141272 A1 | 6/2011 | Uto et al. |
| 2012/0140211 A1 | 6/2012 | Oshima et al. |
| 2012/0194808 A1 | 8/2012 | Oka et al. |
| 2013/0077159 A1 | 3/2013 | Tani |
| 2013/0198697 A1 | 8/2013 | Hotzel |
| 2013/0301040 A1 | 11/2013 | Ahner et al. |
| 2014/0043621 A1 | 2/2014 | Ahner et al. |
| 2014/0098368 A1 | 4/2014 | Ahner et al. |
| 2014/0104604 A1 | 4/2014 | Ahner et al. |
| 2014/0129179 A1 | 5/2014 | Xu et al. |
| 2014/0160481 A1 | 6/2014 | Ahner et al. |
| 2014/0354980 A1 | 12/2014 | Tung et al, |
| 2014/0354981 A1 | 12/2014 | Ahner et al. |
| 2014/0354982 A1 | 12/2014 | Ahner et al. |
| 2014/0354984 A1 | 12/2014 | Tung et al. |
| 2014/0354994 A1 | 12/2014 | Ahner et al. |

FOREIGN PATENT DOCUMENTS

| | | |
|---|---|---|
| JP | 08-178867 A | 7/1996 |
| JP | 2003-202214 | 7/2003 |
| JP | 3692685 B2 | 9/2005 |
| JP | 2006-30851 A | 11/2009 |
| JP | 2011-163872 A | 8/2011 |
| JP | 2012-026862 A | 2/2012 |
| JP | 2012-185121 A | 9/2012 |
| KR | 10-0763942 B1 | 10/2007 |
| KR | 10-0769342 B1 | 10/2007 |
| KR | 10-2011-021304 A | 3/2011 |
| WO | 96-05503 A1 | 2/1996 |

OTHER PUBLICATIONS

Candela CS20, Advanced Inspection for Compound Semiconductor and Optoelectronic Materials, Optical Surface Analyzer, KLA-Tencor Corporation, 2010.
High-sensitivity, High-speed Dark-field Wafer-defect Inspection System—IS3000, Hitachi Review vol. 55, No. 2, pp. 73-77, Hitachi Ltd., 2006.
Hitachi High-Technologies I-5320 / I-6300—Electron Beam Wafer Inspection System, (www.etesters.com/listing/ea101bfb-1422-08df-aaae-08c275a8ee86/I-5320_~_I-6300_-_Electron_Beam_Wafer_Inspection_System), accessed Jun. 19, 2013.
Hitachi High-Technologies IS3000—Dark Field Wafer Defect Inspection System, (www.etesters.com/listing/ea1312b5-1422-08df-aa4b-5fea5982b63b/IS3000_-_Dark_Field_Wafer_Defect_Inspection_System), accessed Jun. 19, 2013.
Hitachi High-Technologies LS6800—Wafer Surface Inspection System, (www.etesters.com/listing/ea1133d4-1422-08df-aad9-258baeaf6c16/LS6800_-_Wafer_Surfce_Inspection_System), accessed Jun. 19, 2103.
LS Unpatterned Wafer Inspection System, (hitachi-htc.ca/products/semiconductor-metrology-equipment/inspections-systems/wafer-inspection-system/ls-unpatterne), accessed Jun. 19, 2013.

* cited by examiner

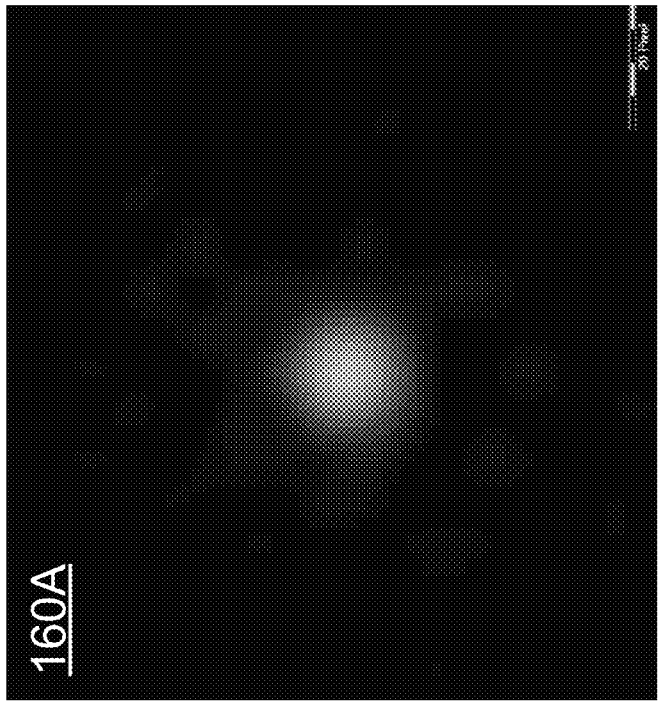
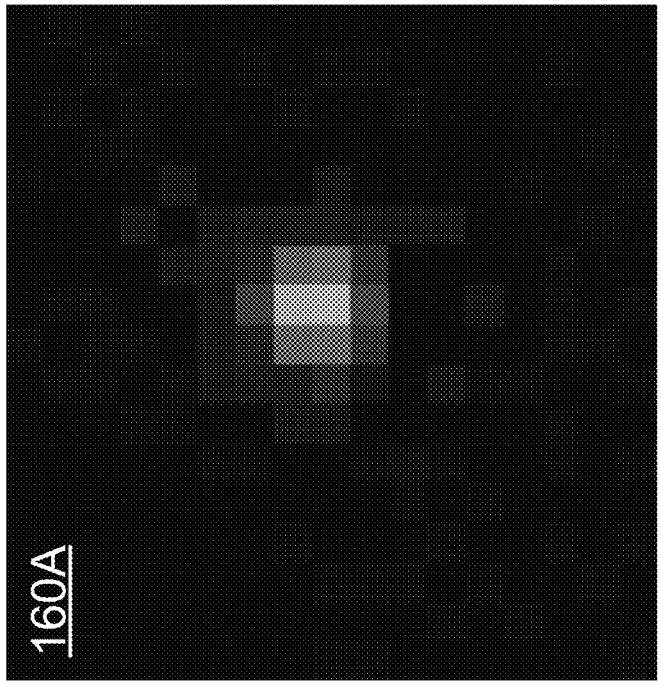
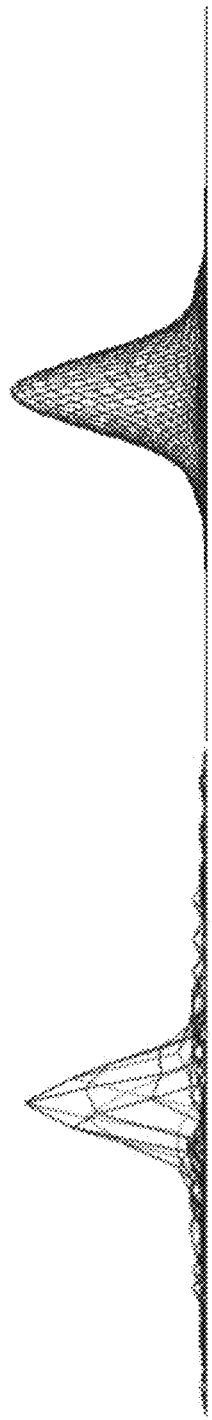
FIG. 6A
FIG. 6B

CLASSIFICATION OF SURFACE FEATURES USING FLUORESCENCE

CROSS REFERENCE

This application claims the benefit of U.S. Provisional Patent Application No. 61/710,666, filed Oct. 5, 2012.

BACKGROUND

An article fabricated on a production line may be inspected for certain features, including defects that might degrade the performance of the article or a system comprising the article. For example, a hard disk for a hard disk drive may be fabricated on a production line and inspected for certain surface features, including surface and subsurface defects that might degrade the performance of the disk or the hard disk drive. Accordingly, apparatuses and methods operable to inspect articles for features such as defects are merited.

SUMMARY

Provided herein is an apparatus, including a photon emitter configured to emit photons onto a surface of an article, a photon detector array configured to receive photons from surface features of the article; and a processing means configured for processing photon-detector-array signals corresponding to photons scattered from the surface features and photons fluoresced from the surface features, wherein the processing means is further configured for classifying the surface features of the article.

These and other features and aspects of the concepts presented herein may be better understood with reference to the following drawings, description, and appended claims.

DRAWINGS

FIG. 1 provides a schematic illustrating detection of surface features of articles in accordance with an embodiment.

Figure 2:
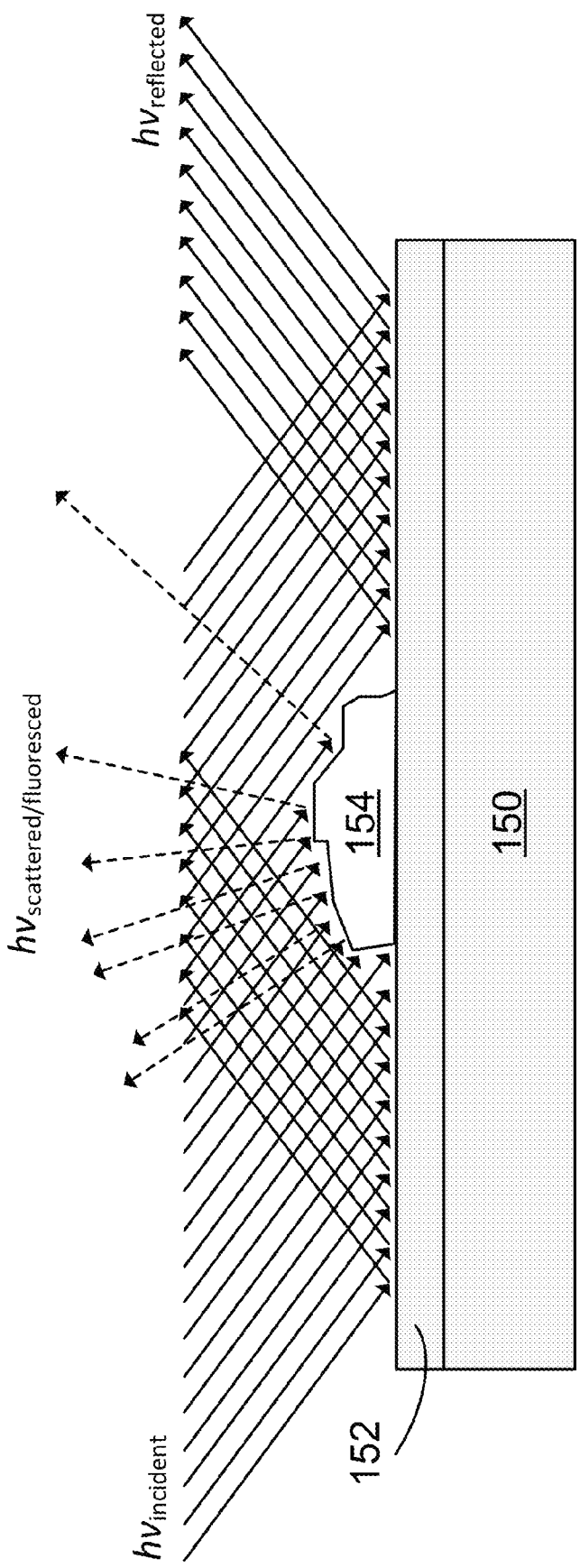

FIG. 2 provides a schematic illustrating photon scattering from a surface feature of an article in accordance with an embodiment.

Figure 3:
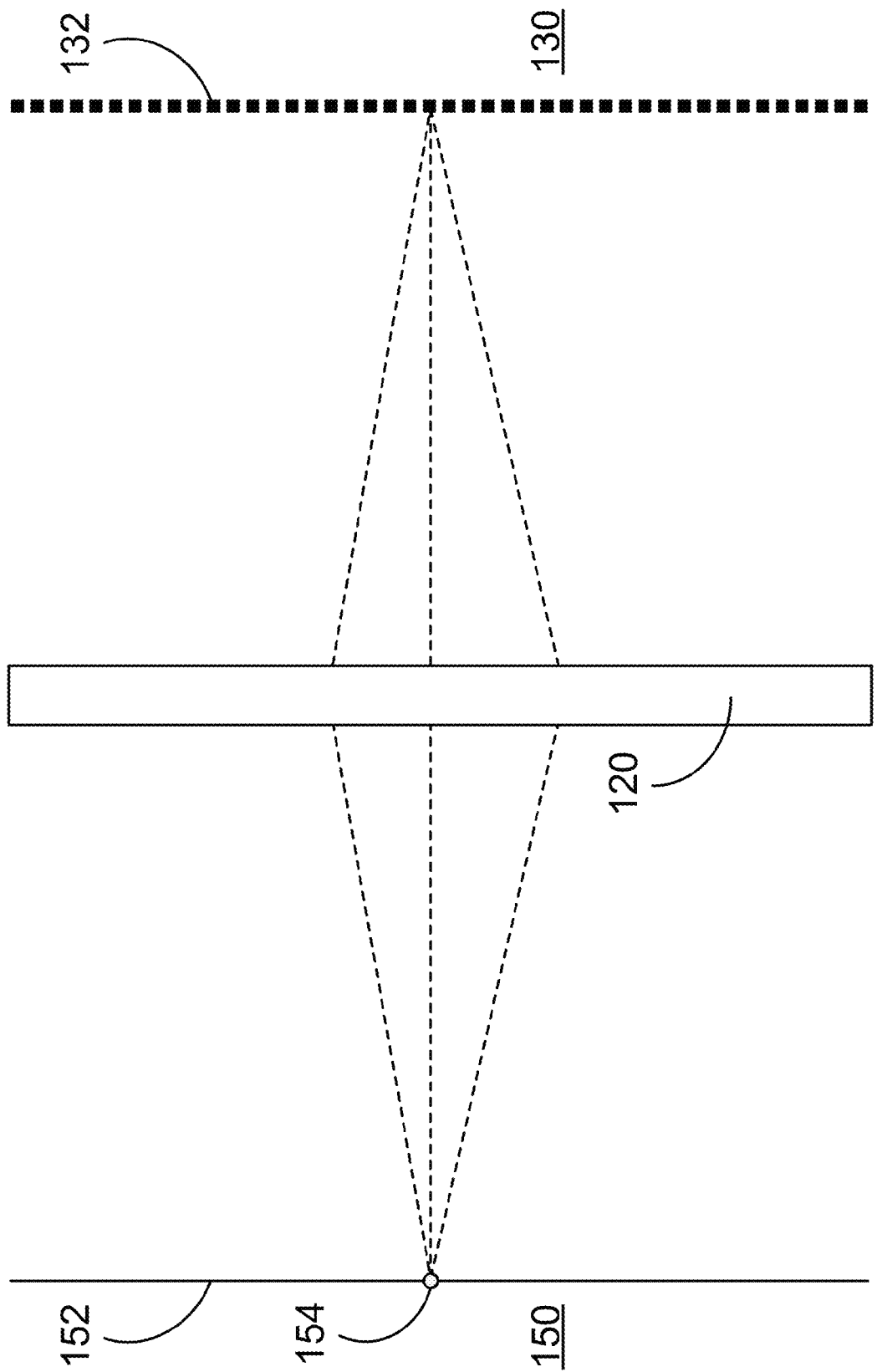

FIG. 3 provides a schematic illustrating photons scattering from a surface feature of an article, through an optical component, and onto a photon detector array in accordance with an embodiment.

Figure 4:
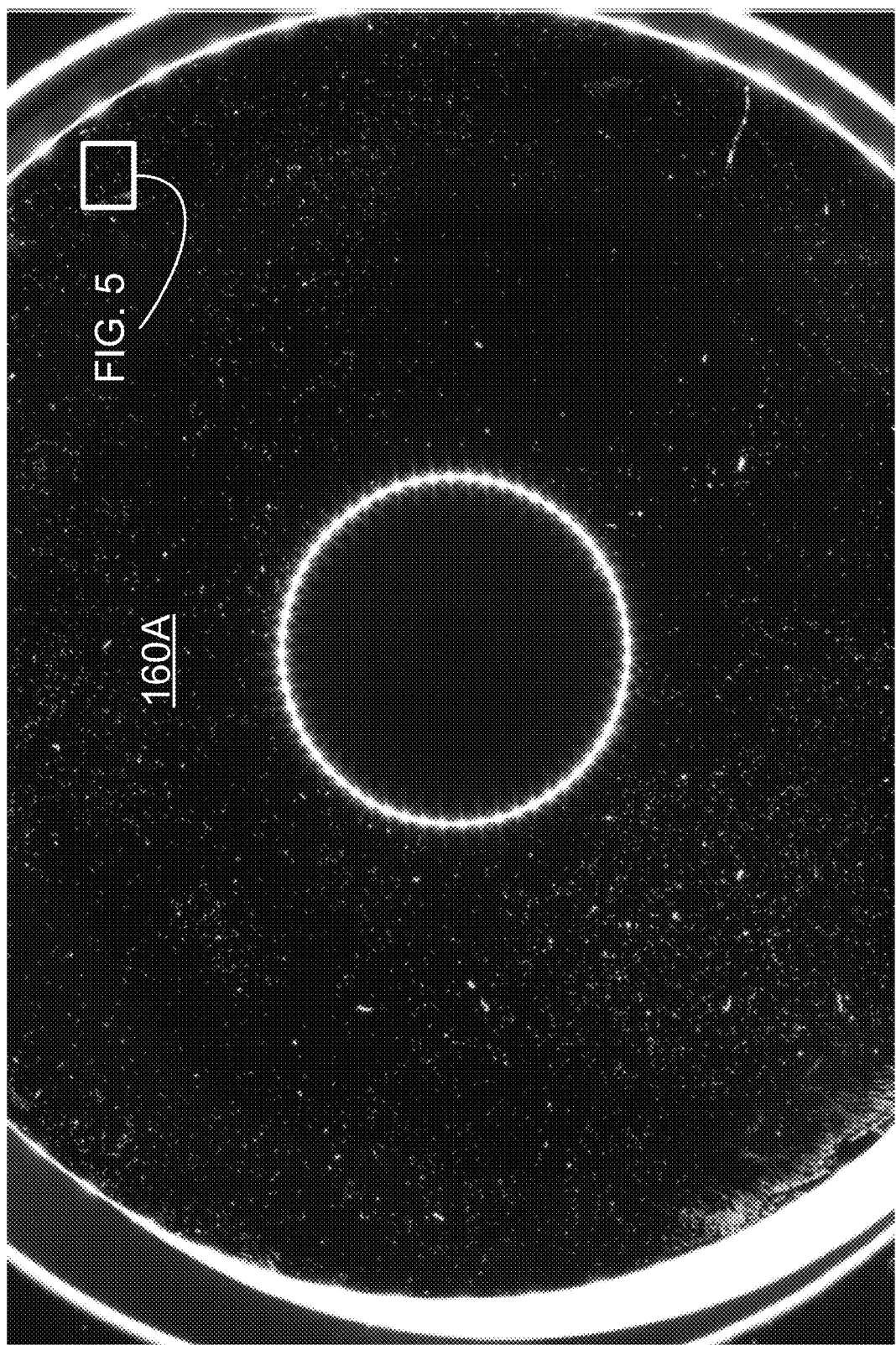

FIG. 4 provides an image of a surface features map of an article in accordance with an embodiment.

Figure 5:
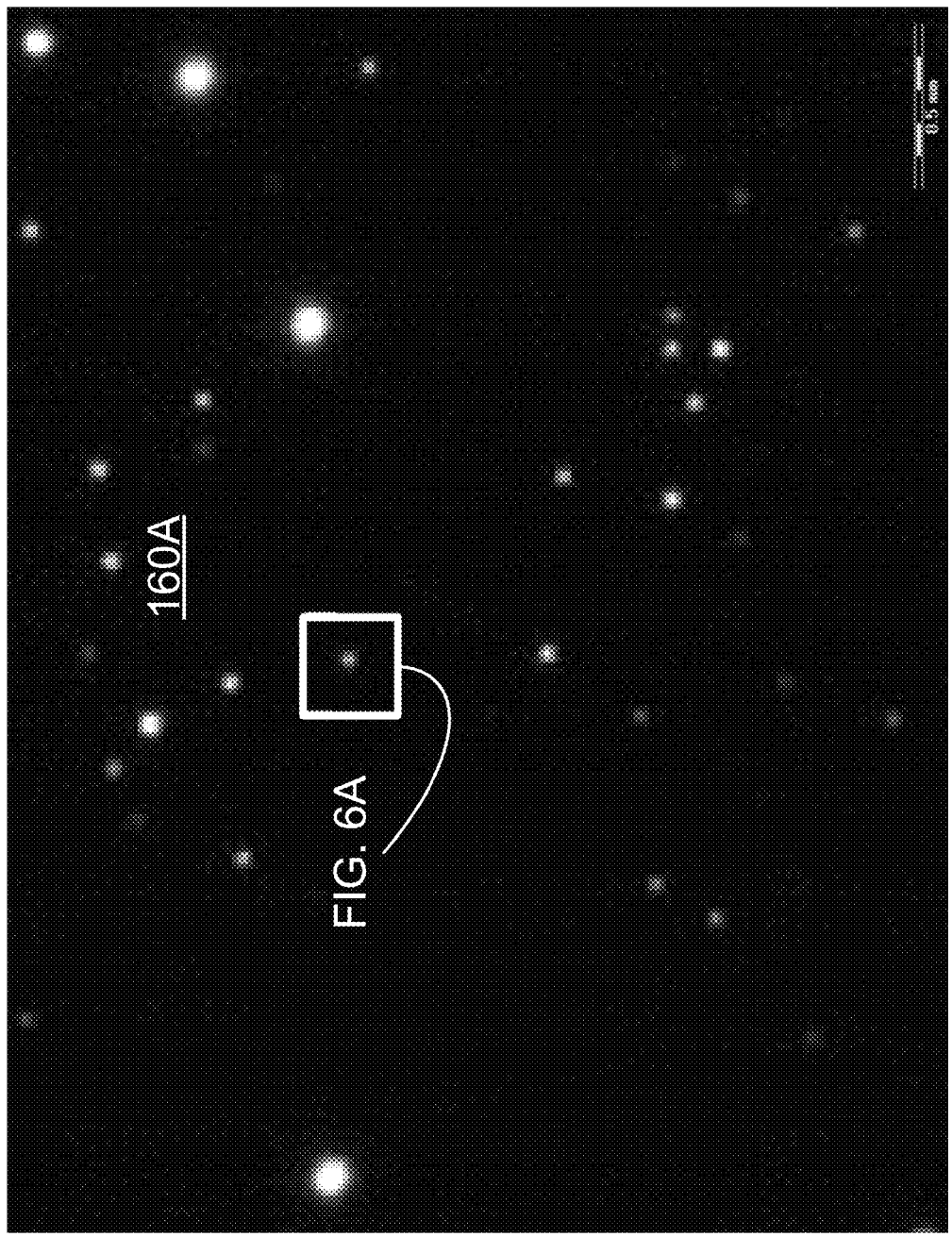

FIG. 5 provides a close-up image of the surface features map provided in FIG. 4.

FIG. 6A (top) provides a close-up image of the surface feature from the map provided in FIG. 5, and FIG. 6A (bottom) provides a photon scattering intensity distribution of the surface feature.

FIG. 6B (top) provides a pixel-interpolated image of the surface feature from FIG. 6A, and FIG. 6B (bottom) provides a pixel-interpolated photon scattering intensity distribution of the surface feature.

Figure 7B:
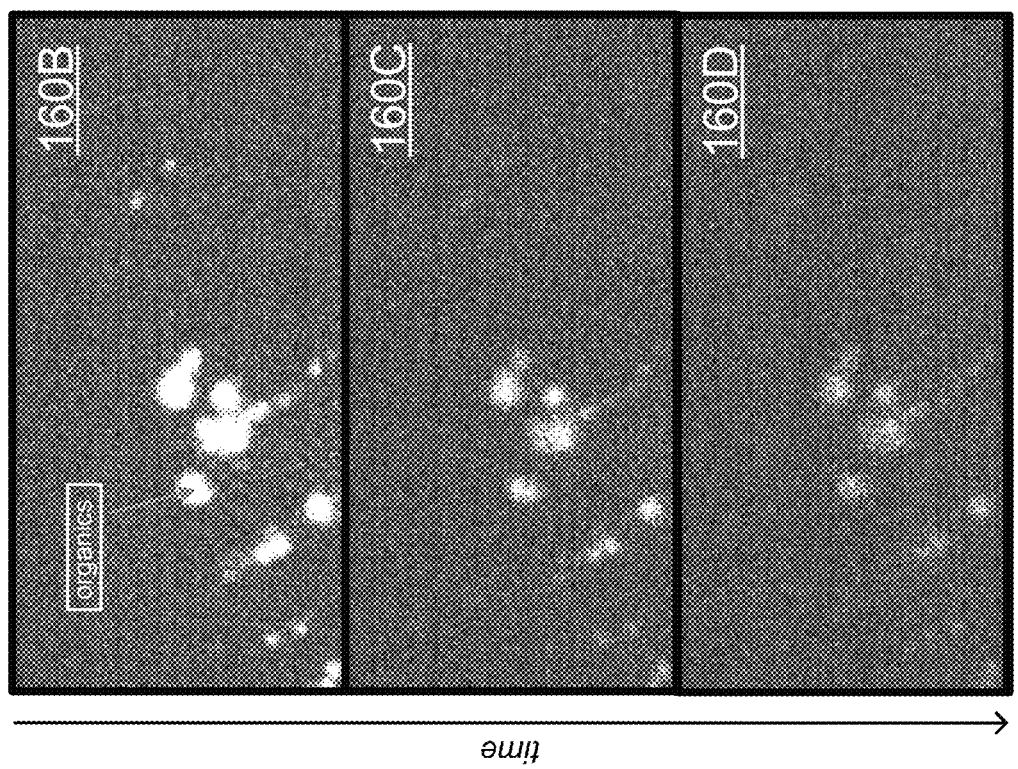
Figure 7A:
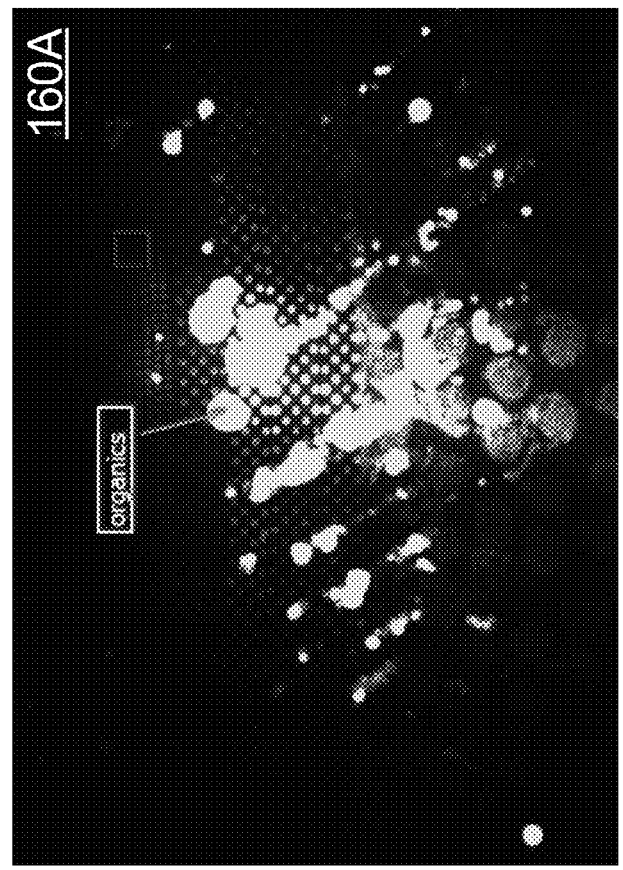

FIG. 7A provides a close-up image of a surface features map having inorganic and organic surface features in accordance with an embodiment.

FIG. 7B provides close-up images of surface features maps showing fluorescence of organic surface features over time in accordance with an embodiment.

Figure 8:
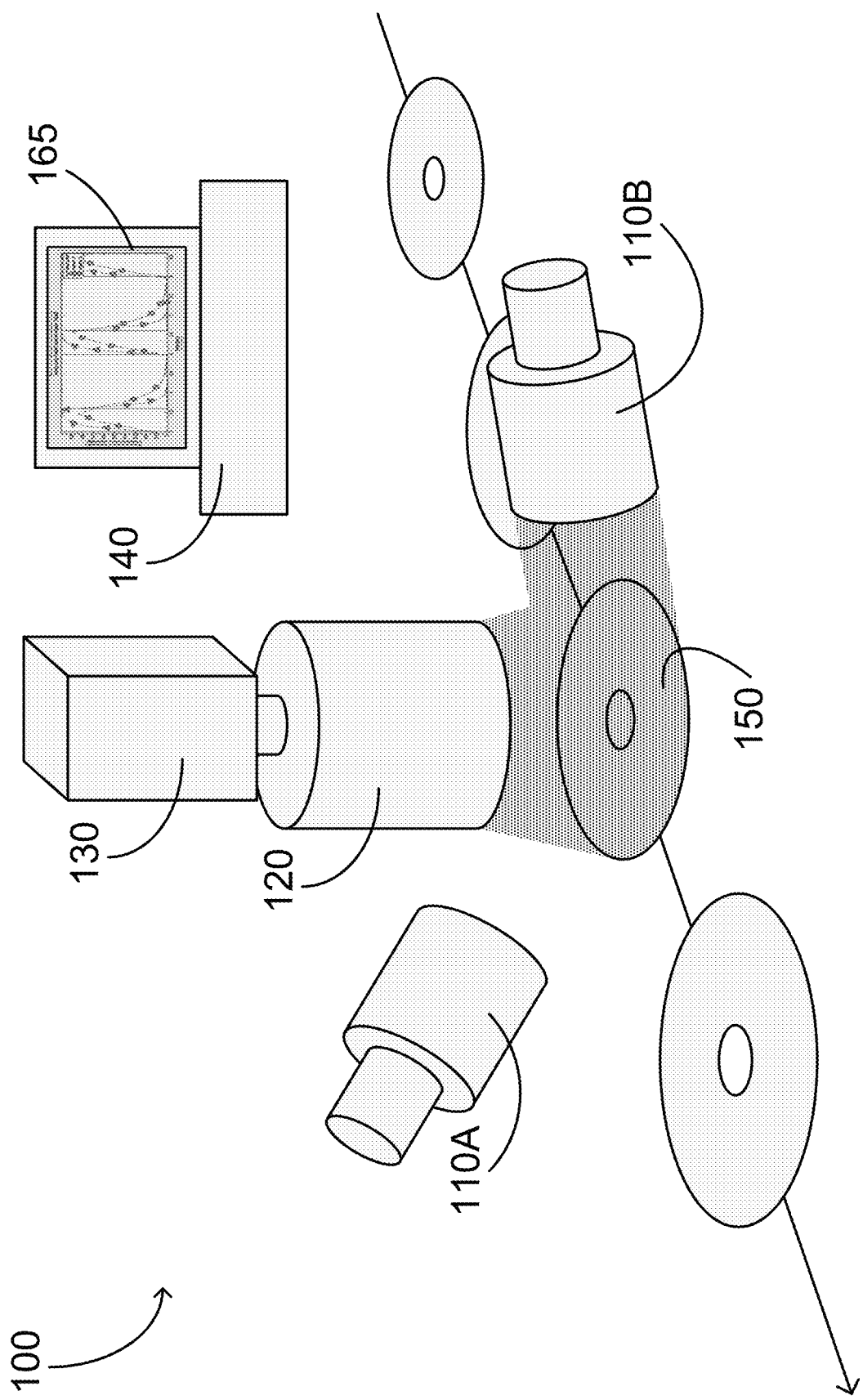

FIG. 8 provides a schematic illustrating detection of surface features of articles in accordance with an embodiment.

Figure 9A:
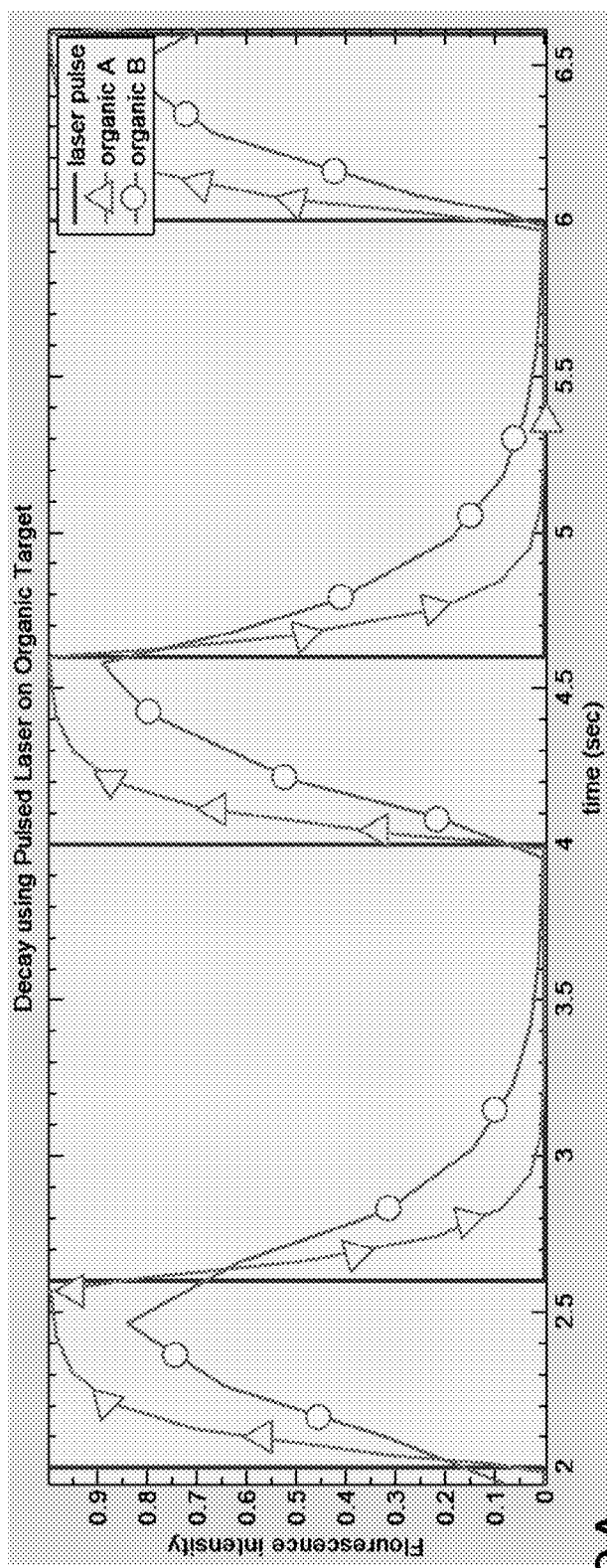

FIG. 9A provides a photon pulse-photon detection scheme in accordance with an embodiment.

Figure 9B:
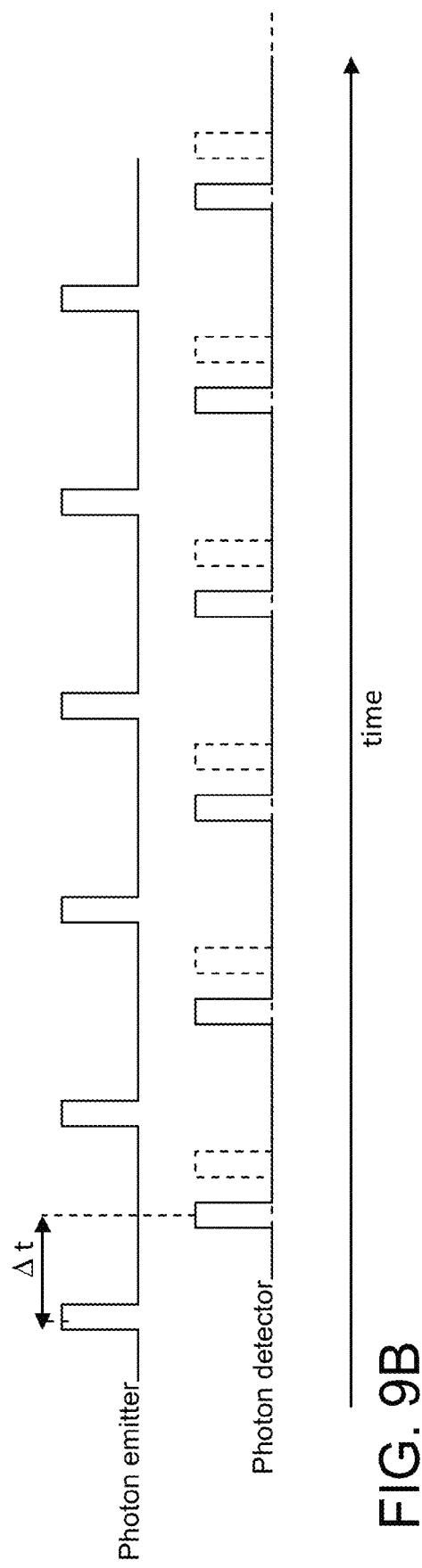

FIG. 9B provides a plot of fluorescence intensity vs. time for a photon pulse-photon detection scheme in accordance with an embodiment.

DESCRIPTION

Before some particular embodiments are described in greater detail, it should be understood by persons having ordinary skill in the art that the particular embodiments described and/or illustrated herein do not limit the concepts presented herein, as elements in such particular embodiments may vary. It should likewise be understood that a particular embodiment described and/or illustrated herein has elements which may be readily separated from the particular embodiment and optionally combined with any of several other embodiments or substituted for elements in any of several other embodiments described herein.

It should also be understood by persons having ordinary skill in the art that the terminology used herein is for the purpose of describing some particular embodiments, and the terminology does not limit the concepts presented herein. Unless indicated otherwise, ordinal numbers (e.g., first, second, third, etc.) are used to distinguish or identify different elements or steps in a group of elements or steps, and do not supply a serial or numerical limitation. For example, "first," "second," and "third" elements or steps of embodiments need not necessarily appear in that order, and embodiments need not necessarily be limited to the three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art.

An article fabricated on a production line may be inspected for certain features, including defects that might degrade the performance of the article or a system comprising the article. For example, a hard disk for a hard disk drive may be fabricated on a production line and inspected for certain surface features, including surface and subsurface defects that might degrade the performance of the disk or the hard disk drive. Provided herein are apparatuses and methods for inspecting articles to detect, map, and/or characterize certain surface features such as surface and/or subsurface defects. Embodiments of the invention will now be described in greater detail.

With respect to articles that may be inspected with apparatuses and methods herein, such articles include any article of manufacture or a workpiece thereof in any stage of manufacture having one or more optically smooth surfaces, examples of which include, but are not limited to, semiconductor wafers, magnetic recording media (e.g., hard disks for hard disk drives), and workpieces thereof in any stage of manufacture. Such articles may be inspected for certain surface features, including surface and/or subsurface defects that might degrade the performance of the article, which surface and/or subsurface defects include particle and stain contamination, as well as defects including scratches and voids. In order to characterize the foregoing features, which is an important step in root cause failure analysis, a number of analyses on different analytical apparatuses is typically required, including optical analysis and subsequent analysis using, for example, one or more of atomic force microscopy ("AFM"), scanning electron microscopy ("SEM")/Energy Dispersive X-Ray ("EDX"); and Raman spectroscopy. The number of analyses on different analytical apparatuses, and the time required for each analysis can be very time consuming, which limits throughput in root cause failure analysis. The apparatuses and methods provided herein for inspecting articles to detect, map, and/or characterize certain surface features reduces the number of different analytical apparatuses and the time required for each analysis, which increases throughput for root cause failure analysis.

FIG. 1 provides a schematic for detecting, mapping, and/or characterizing surface features of articles, illustrating an apparatus 100 comprising a photon emitter 110A, an optical setup 120, a photon detector array 130, and a computer or equivalent device 140, as well as an article 150 and a surface features map 160A of a surface of the article 150, in accordance with an embodiment. In such an embodiment, the photon detector array 130 may be configured to receive photons (originally emitted from the photon emitter 110A) scattered from surface features of the article 150 for a surface features map 160A (see also surface features map 160A of FIG. 7A). The same photon detector array 130, or a different photon detector array, may be configured to subsequently receive photons fluoresced from surface features of the article 150 for one or more additional surface features maps (e.g., 160B, 160C, and/or 160D of FIG. 7B). Differential surface features maps 160A and 160B, as well as any additional surface features maps (e.g., 160C, 160D . . . 160n, wherein the index n indicates the n$^{th}$ surface features map), or the information sufficient to produce such surface features maps, may be used to characterize surface features of articles and/or differentiate surface features of articles. For example, differential surface features maps 160A and 160B, as well as any additional surface features maps (e.g., 160C, 160D . . . 160n, wherein the index n indicates the n$^{th}$ surface features map), or the information sufficient to produce such surface features maps, may be used to differentiate between inorganic and organic surface features of articles. The articles and apparatuses of the invention, as well as methods of the invention, are not limited to the embodiment in FIG. 1, as additional embodiments of the invention may be realized by the features described in more detail herein.

An apparatus for detecting, mapping, and/or characterizing surface features of articles may comprise a single photon emitter (e.g., see photon emitter 110A of FIG. 1) or a plurality of photon emitters (e.g., see photon emitters 110A and 110B of FIG. 8). In some embodiments, for example, the apparatus may comprise at least 1, 2, 3, 4, 5, 6, 7, 8, 9, or 10 photon emitter(s). In some embodiments, for example, the apparatus may comprise no more than 10, 9, 8, 7, 6, 5, 4, 3, 2, or 1 photon emitter(s). Combinations of the foregoing may also be used to describe the number of photon emitters of the apparatus. In some embodiments, for example, the apparatus may comprise at least 2 photon emitters and no more than 10 photon emitters (e.g., between 2 and 10 photon emitters), such as at least 2 photon emitters and no more than 6 photon emitters (e.g., between 2 and 6 photon emitters), including at least 2 photon emitters and no more than 4 photon emitters (e.g., between 2 and 4 photon emitters). A single photon emitter may be used to emit photons onto a surface of an article, such as the entire surface of the article or some predetermined portion of the surface of the article (e.g., for gradational rotation of the article for piecewise inspection, if desired); each photon emitter of a plurality of photon emitters may be used to emit photons onto the surface of the article, such as the entire surface of the article or some predetermined portion of the surface of the article, at different times and/or at the same time in any collection. Further with respect to the plurality of photon emitters, each photon emitter of a plurality of photon emitters may be the same or different, or some combination thereof (e.g., at least 2 of the same photon emitter, with the remainder of photon emitters being different; at least 4 of the same photon emitter, with the remainder of photon emitters being different; etc.). In some embodiments, for example, the apparatus may comprise at least two different photon emitters, wherein the two different photon emitters are each separately configured to emit photons onto a surface of an article, such as the entire surface of the article or some predetermined portion of the surface of the article. FIG. 8, which is described in more detail herein, provides a schematic illustrating detection of surface features of articles in accordance with such embodiment.

Whether the apparatus comprises a single photon emitter or a plurality of photon emitters, each photon emitter may emit photons onto a surface of an article at a distance and/or an angle optimized for one or more types of features, which types of features are described in more detail herein. The angle optimized for one or more types of features may be equal to the glancing angle, which glancing angle is the complement of the angle of incidence, and which angle of incidence is the angle between a ray comprising the emitted photons incident on the surface of the article and the normal (i.e., a line perpendicular to the surface of the article) at the point at which the ray is incident. The glancing angle may also be described as the smallest angle between a ray comprising the emitted photons incident on the surface of the article and the surface at the point at which the ray is incident.

FIG. 2 provides a number of rays comprising emitted photons incident on a surface 152 of an article 150 that form a glancing angle with the surface 152. FIG. 2 further provides a number of rays comprising reflected photons that form an angle of reflection with the normal to the surface, which angle of reflection is equal to the angle of incidence. FIG. 2 even further provides a number of rays comprising scattered photons or fluoresced photons from a feature 154 on the surface 152 of the article 150, which rays comprising scattered photons or fluoresced photons respectively form various scatter angles or emission angles. A photon emitter may emit photons at a glancing angle ranging from 0° to 90°, wherein a glancing angle of 0° represents the photon emitter emitting photons onto the surface of the article from a side of the article, and wherein a glancing angle of 90° represents the photon emitter emitting photons onto the surface of the article from directly above the article. In some embodiments, for example, a photon emitter may emit photons onto a surface of an article such that the glancing angle is at least 0°, 5°, 10°, 15°, 20°, 25°, 30°, 35°, 40°, 45°, 50°, 55°, 60°, 65°, 70°, 75°, 80°, 85°, or 90°. In some embodiments, for example, a photon emitter may emit photons onto a surface of an article such that the glancing angle is no more than 90°, 85°, 80°, 75°, 70°, 65°, 60°, 55°, 50°, 45°, 40°, 35°, 30°, 25°, 20°, 15°, 10°, 5°, or 0°. Combinations of the foregoing may also be used to describe the glancing angle at which a photon emitter may emit photons onto a surface of an article. In some embodiments, for example, a photon emitter may emit photons onto a surface of an article such that the glancing angle is at least a 0° and no more than 90° (i.e., between 0° and 90°), such as least 0° and no more than 45° (i.e., between 0° and 45°), including at least 45° and no more than 90° (i.e., between 45° and 90°).

A photon emitter may emit photons onto a surface of an article, such as the entire surface or some predetermined portion of the surface (e.g., for gradational rotation of the article for piecewise inspection, if desired). The photon emitter may further emit photons onto the entire surface of the article or some predetermined portion of the surface such that the entire surface or the predetermined portion of the surface is uniformly or homogenously illuminated. Uniformly illuminating the entire surface of the article or some predetermined portion of the surface includes, but is not limited to, subjecting the entire surface of the article or some predetermined portion of the surface of the article to the same or about the same photon energy per unit time (e.g., photon power or photon flux) and/or photon power per unit area (e.g., photon flux density). In radiometric terms, uniformly illuminating includes, but is not limited to, subjecting the entire surface of the article or some predetermined portion of the surface of the article to the same or about the same radiant energy per unit time (e.g., radiant power or radiant flux) and/or radiant power per unit area (e.g., irradiance or radiant flux density).

With the appreciation that photons are the elementary particles of electromagnetic radiation or light, a photon emitter or light source may provide light comprising a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light comprising a relatively wide range of frequencies (e.g., whole spectrum, broad spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. A photon emitter or light source may be used in conjunction with one or more optical components of an optical setup to provide light having any of the foregoing qualities.

In view of the foregoing, a photon emitter or light source may comprise a lamp such as a flash lamp, including a high-speed flash lamp, configured to minimize vibration while detecting photons scattered from surface features of an article with a photon detector array. In some embodiments, for example, a photon emitter or light source may comprise a high-speed Xe flash lamp such as a 500 W Xe flash lamp to minimize vibration while detecting photons scattered from surface features of an article with a photon detector array.

Also in view of the foregoing, a photon emitter or light source may comprise a collimated light source such as a laser, including a combination of lasers, configured to emit photons onto a surface of an article at one or more angles. In some embodiments, for example, a combination of lasers may be provided to a laser beam shaper such that the combination of lasers emits photons onto a surface of an article at one angle. In some embodiments, for example, a combination of lasers may be provided to a laser beam shaper such that the combination of lasers emits photons onto a surface of an article at multiple angles. In some embodiments, for example, at least 2, 4, 6, 8, 10, 12, 14, 16, 18, 20, 22, 24, 26, 28, or 30 lasers, or even more than 30 lasers, may be provided to a laser beam shaper such that the combination of lasers emits photons onto a surface of an article at one or more angles. In some embodiments, for example, no more than 30, 28, 26, 24, 22, 20, 18, 16, 14, 12, 10, 8, 6, 4, or 2 lasers may be provided to a laser beam shaper such that the combination of lasers emits photons onto a surface of an article at one or more angles. Combinations of the foregoing may also be used to describe combinations of lasers provided to a laser beam shaper. In some embodiments, for example, at least 2 lasers and no more than 30 lasers (e.g., between 2 and 30 lasers), such as at least 10 lasers and no more than 30 lasers (e.g., between 10 and 30 lasers), including at least 20 lasers and no more than 30 lasers (e.g., between 20 and 30 lasers), and further including at least 24 lasers and no more than 28 lasers (e.g., between 24 and 28 lasers) may be provided to a laser beam shaper such that the combination of lasers emits photons onto a surface of an article of an article at one or more angles.

Further in view of the foregoing, a photon emitter or light source may comprise a two-dimensional light source such as a combination of point light sources, including a linear combination or array, an arcuate combination or array, etc. of point light sources configured to emit photons onto a surface of an article. In some embodiments, for example, a two-dimensional light source may comprise a combination of at least 10, 20, 40, 60, 80, 100, 110, 120, 140, 160, 180, or 200 point light sources, or even more than 200 point sources. In some embodiments, for example, a two-dimensional light source may comprise a combination of no more than 200, 180, 160, 140, 120, 100, 80, 60, 40, 20, or 10 point light sources. Combinations of the foregoing may also be used to describe two-dimensional light sources comprising combinations of point light sources. In some embodiments, for example, a two-dimensional light source may comprise a combination of at least 10 and no more than 200 (e.g., between 10 and 200) point light sources, such as at least 40 and no more than 160 (e.g., between 40 and 160) point light sources, including at least 60 and no more than 140 (e.g., between 60 and 140) point light sources, and further including at least 80 and no more than 120 (e.g., between 80 and 120) point light sources. Such point light sources may be linearly combined to form a two-dimensional light source such as a strip light. Such point light sources may be arcuately combined to form a two-dimensional light source such as a ring light. In some embodiments, for example, a photon emitter or light source may comprise a two-dimensional light source comprising at least 60 point light sources, such as a ring light comprising at least 60 point light sources, including a ring light comprising at least 60 light-emitting diodes ("LEDs"), and further including a ring light comprising at least 100 LEDs. A two-dimensional light source comprising LEDs may comprise white LEDs, wherein each LED has a power of at least 10 mW. An LED-based ring light may enhance features such as scratches (e.g., circumferential scratches) and/or voids in surfaces of articles, especially when the LED-based ring light is configured to emit photons onto the surfaces of the articles with lower angles (e.g., glancing angle equal to or less than 45°).

The apparatus may further comprise an optical setup (e.g., see optical setup 120 of FIG. 1), which optical setup may manipulate photons emitted from one or more photon emitters and/or photons scattered or fluoresced from surface features of articles. With the appreciation that photons are the elementary particles of electromagnetic radiation or light, the optical setup may manipulate light emitted from one or more photon emitters and/or light scattered or fluoresced from surface features of articles. The optical setup up may comprise any of a number of optical components placed in the optical path before an article such that the optical components may be used to manipulate photons emitted from one or more photon emitters before uniformly or homogenously illuminating the entire surface or the predetermined portion of the surface of the article. Alternatively, or in addition, the optical setup up may comprise any of a number of optical components placed in the optical path after an article such that the optical components may be used to manipulate photons scattered or fluoresced from surface features of the article. The forgoing optical components may include, but are not limited to, optical components such as lenses, filters, gratings, and mirrors.

With respect to optical components such as lenses, the optical setup may comprise a single lens or a plurality of lenses, including, but not limited to, a combination of a lens coupled to a photon detector array (e.g., photon detector array 130 of FIG. 1) for collecting and detecting photons scattered from surface features of an article. The lens coupled to the photon detector array may be an objective lens, such as a telecentric lens, including an object-space telecentric lens (i.e., entrance pupil at infinity), an image-space telecentric lens (i.e., exit pupil at infinity), or a double telecentric lens (i.e., both pupils at infinity). Coupling a telecentric lens to a photon detector array reduces errors with respect to the position of surface features of articles, reduces distortion of surface features of articles, and/or enables quantitative analysis of photons scattered from surface features of articles, which quantitative analysis includes integration of photon scattering intensity distribution for size determination of surface features of articles. Additional optical components, such as lenses, filters, gratings, and mirrors, may be placed in any combination of one or more optical components at or near the entrance pupil of the lens coupled to the photon detector array, at or near the exit pupil of the lens coupled to the photon detector array (i.e., in-between the exit pupil of the lens and the photon detector array), or some combination thereof to manipulate photons scattered or fluoresced from surface features of the article.

With respect to optical components such as filters, the optical setup may comprise a filter or a plurality of filters including, but not limited to, wavelength filters, band-pass filters, polarization filters, coherence filters, and phase filters or waveplates. Wavelength filters, for example, may be used in conjunction with a photon emitter or light source to provide light comprising a relatively wide range of wavelengths or frequencies, a relatively narrow range of wavelengths or frequencies, or a particular wavelength or frequency. Polarization filters, for example, may also be used in conjunction with a photon emitter or light source to provide light of a desired polarization including polarized light, partially polarized light, or nonpolarized light. When one or more of the foregoing filters is placed in the optical path after an article to manipulate photons scattered or fluoresced from surface features of the article, the one or more filters may be further used to extract chemical signatures from surface features of the article and/or to characterize surface features of the article.

To detect photons scattered or fluoresced from surface features of articles, an apparatus may further comprise a single photon detector array (e.g., see photon detector array 130 of FIG. 1) comprising a plurality of photon detectors or a plurality of photon detector arrays, each comprising a plurality of photon detectors. In some embodiments, for example, the plurality of photon detector arrays may comprise at least 2, 3, 4, 5, 6, 7, 8, 9, or 10 photon detector arrays. In some embodiments, for example, the plurality of photon detector arrays may comprise no more than 10, 9, 8, 7, 6, 5, 4, 3, or 2 photon detector arrays. Combinations of the foregoing may also be used to describe the plurality of photon detector arrays. In some embodiments, for example, the plurality of photon detector arrays may comprise at least 2 photon detector arrays and no more than 10 photon detector arrays (e.g., between 2 and 10 photon detector arrays), such as at least 2 photon detector arrays and no more than 5 photon detector arrays (e.g., between 2 and 5 photon detector arrays). Further with respect to the plurality of photon detector arrays, each photon detector array of the plurality of photon detector arrays may be the same or different, or some combination thereof (e.g., at least 2 of the same photon detector array, with the remainder of photon detector arrays being different; at least 3 of the same photon detector array, with the remainder of photon detector arrays being different; etc.).

Whether the apparatus comprises a single photon detector array or a plurality of photon detector arrays, each photon detector array may be oriented to detect photons scattered or fluoresced from surface features of an article at a distance and/or an angle for an optimum acceptance of photons (e.g., maximum acceptance of photons with minimum background noise) scattered or fluoresced from one or more types of features, which types of features are described in more detail herein. Likewise, a photon-detector-array-and-lens (e.g., telecentric lens) combination may be oriented to collect and detect photons scattered or fluoresced from surface features of an article at a distance and/or an angle for an optimum acceptance of photons scattered from one or more types of features. Such an angle may be the angle between a ray comprising the center line axis of the photon detector array and/or the lens extended to the surface of the article and the normal (i.e., a line perpendicular to the surface of the article) at the point at which the ray is extended. The angle, optionally in combination with an aperture that may be variably sized to accept a larger or smaller angle of scattered photons or fluoresced photons (e.g., for differential surface feature maps), or optionally in combination with an aperture that may be optimally sized for maximum acceptance of scattered photons or fluoresced photons with minimum background noise, may allow for acceptance of scattered photons or fluoresced photons respectively having a plurality of scatter angles or emission angles, which scattered photons or fluoresced photons may respectively be scattered or fluoresced from one or more types of features. A scatter angle or emission angle may be different than the angle of reflection, which angle of reflection is equal to the angle of incidence as described herein. FIG. 2 provides a number of rays comprising photons scattered or fluoresced from a feature 154 on a surface 152 of an article 150, which rays represent various scatter angles.

In view of the foregoing, a photon detector array or photon-detector-array-and-lens combination may be oriented at an angle ranging from 0° to 90°, inclusive, wherein an angle of 0° represents orientation of the photon detector array or the photon-detector-array-and-lens combination at a side of the article, and wherein an angle of 90° represents orientation of the photon detector array or photon-detector-array-and-lens combination directly above the article. In some embodiments, for example, a photon detector array or photon-detector-array-and-lens combination may be oriented at an angle of at least 0°, 5°, 10°, 15°, 20°, 25°, 30°, 35°, 40°, 45°, 50°, 55°, 60°, 65°, 70°, 75°, 80°, 85°, or 90°. In some embodiments, for example, a photon detector array or photon-detector-array-and-lens combination may be oriented at an angle of no more than 90°, 85°, 80°, 75°, 70°, 65°, 60°, 55°, 50°, 45°, 40°, 35°, 30°, 25°, 20°, 15°, 10°, or 5°, or 0°. Combinations of the foregoing may also be used to describe the angle at which the photon detector array or photon-detector-array-and-lens combination may be oriented. In some embodiments, for example, a photon detector array or photon-detector-array-and-lens combination may be oriented at an angle of at least a 0° and no more than a 90° (i.e., between 0° and) 90°, such as least 0° and no more than 45° (i.e., between 0° and 45°) or at least 45° and no more than 90° (i.e., between 45° and 90°).

The photon detector array, optionally in combination with a lens (e.g., telecentric lens), may detect photons scattered or fluoresced from surface features of an article, such as the entire surface of the article or some predetermined portion of the surface of the article. The photon detector array, optionally in combination with a lens (e.g., telecentric lens), may detect photons scattered or fluoresced from surface features of an article, such as the entire surface of the article or some predetermined portion of the surface of the article, while oriented at a distance and/or an angle for an optimum acceptance of photons (e.g., maximum acceptance of photons with minimum background noise) scattered or fluoresced from one or more types of features. As provided herein, the angle for an optimum acceptance of photons scattered or fluoresced from one or more types of features may allow for acceptance of scattered photons or fluoresced photons respectively having a plurality of scatter angles or emission angles, which scattered photons or fluoresced photons may respectively be scattered or fluoresced from one or more types of features.

With the appreciation that photons are the elementary particles of electromagnetic radiation or light, a photon detector array or light detector array may detect light comprising a relatively wide range of wavelengths (e.g., whole spectrum, broad spectrum, ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light comprising a relatively wide range of frequencies (e.g., whole spectrum, broad spectrum, ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. As discussed herein, a photon detector array or light detector array may be used in conjunction with one or more optical components of an optical setup to detect light having any of the foregoing qualities.

The photon detector array may comprise a plurality of pixel sensors, which pixel sensors, in turn, may each comprise a photon detector (e.g., a photodiode) coupled to a circuit comprising a transistor configured for amplification. Features of a photon detector array comprising such pixel sensors include, but are not limited to, low temperature operation (e.g., down to −40° C.), low electron noise (e.g., 2-10 e⁻ RMS; 1 e⁻ RMS; <1 e⁻ RMS; etc.), wide dynamic range (e.g., 30,000:1, 8,500:1; 3,000:1; etc.), and/or decreased photon/light collection time. A photon detector array may comprise a large number of pixel sensors (e.g., ≥1,000,000 or ≥1 M pixel sensors) arranged in rows and columns of a two-dimensional array, wherein each pixel sensor comprises a photon detector coupled to an amplifier. In some embodiments, for example, a photon detector array may comprise at least 1 M, 2M, 3M, 4M, 5M, 6M, 7M, 8M, 9M, 10M, or more, pixel sensors arranged in rows and columns of a two-dimensional array. In some embodiments, for example, a photon detector array may comprise no more than 10 M, 9M, 8M, 7M, 6M, 5M, 4M, 3M, 2M, or 1M, pixel sensors arranged in rows and columns of a two-dimensional array. Combinations of the foregoing may also be used to describe the number of pixel sensors in a photon detector array. In some embodiments, for example, a photon detector array may comprise at least 1M and no more than 10M (e.g., between 1 M and 10M) pixel sensors arranged in rows and columns of a two-dimensional array, such as at least 1M and no more than 8M (e.g., between 1M and 8M) pixel sensors, including at least 1M and no more than 6M (e.g., between 1M and 8M) pixel sensors, further including at least 2M and no more than 6M (e.g., between 1 M and 8M) pixel sensors, and even further including at least 2M and no more than 5M (e.g., between 2M and 5M) pixel sensors.

Due to surface reflections of surface features of articles and/or small angle scattering (e.g., 4π scattering), surface features may appear much larger in size enabling pixel sensors larger the than surface features to be used. In some embodiments, for example, a photon detector array may comprise micrometer-sized (i.e., admits of μm units as measured) pixel sensors at least 1 μm, 2 μm, 3 μm, 4 μm, 5 μm, 6 μm, 7 μm, 8 μm, 9 μm, or 10 μm in their smallest dimension. In some embodiments, for example, a photon detector array may comprise micrometer-sized pixel sensors no more than 10 μm, 9 μm, 8 μm, 7 μm, 6 μm, 5 μm, 4 μm, 3 μm, 2 μm, or 1 μm in their smallest dimension. Combinations of the foregoing may also be used to describe dimensions of micrometer-sized pixel sensors in photon detector arrays. In some embodiments, for example, a photon detector array may comprise micrometer-sized pixel sensors at least 1 μm and no more than 10 μm (e.g., between 1 μm and 10 μm) in their smallest dimension, such as at least 1 μm and no more than 7 μm (e.g., between 1 μm and 7 μm), including at least 4 μm and no more than 10 μm (e.g., between 4 μm and 10 μm), and further including at least 4 μm and no more than 7 μm (e.g., between 4 μm and 7 μm). Such micrometer-sized pixel sensors may be used in the apparatus to detect, map, and/or characterize surface features of articles that are more than 100 times smaller than the micrometer-sized pixel sensors.

In view of the foregoing, the single photon detector array or the plurality of photon detector arrays may each comprise a complementary metal-oxide semiconductor ("CMOS") or a scientific complementary metal-oxide semiconductor ("sCMOS"), each of which may optionally be part of CMOS camera or a sCMOS camera, respectively. Alternatively, the single photon detector array or the plurality of photon detector arrays may each comprise a charge-coupled device ("CCD"), which may optionally be part of CCD camera. While a CCD-based photon detector array might have a slower recording speed than a CMOS-based or sCMOS-based photon detector array, a CCD-based photon detector array may be desirable in applications requiring less electronic and/or image noise. A CCD-based photon detector array, including an electron-multiplying CCD ("EMCCD"), may also be desirable in certain applications having low-light conditions, such as detecting photons fluoresced from surface features of articles. Furthermore, a plurality of photon detector arrays is not limited to combinations of either CMOS/sCMOS-based photon detector arrays or CCD-based photon-detector arrays, as a plurality of photon detector arrays may comprise a combination of any of a number of CMOS/sCMOS-based photon detector arrays and CCD-based photon-detector arrays in applications that benefit from employing each type of technology. In some embodiments, for example, a CMOS/sCMOS-based photon detector array may be used to detect photons scattered from surface features of articles while a CCD/EMCCD-based photon detector array may be used to detect photons fluoresced from surface features of articles.

FIG. 3 provides a schematic for detection of surface features of an article, illustrating a close-up, cross-sectional view of an apparatus comprising an optical setup and a photon detector array. As shown, article 150 comprises a surface 152 and at least surface feature 154. Photons may be scattered or fluoresced by the surface feature 154 and collected and detected by a combination comprising an optical setup 120 coupled to a photon detector array 130, which combination may be placed at a distance and/or an angle for a an optimum acceptance of photons (e.g., maximum acceptance of photons with minimum background noise) scattered or fluoresced from one or more types of features. The optical setup 120, which may comprise a telecentric lens, may collect and focus the photons scattered or fluoresced from the surface feature 154 onto one or more pixel sensors 132 of photon detector array 130, which one or more pixel sensors may each comprise a photon detector coupled to an amplifier (e.g., CMOS/sCMOS-based photon detector array; EMCCD-based photon detector array; etc.). The one or more pixel sensors 132, each of which corresponds to a particular, fixed area of an article's surface and a pixel in a map of the article's surface features, may provide one or more signals to a computer or equivalent device for mapping or otherwise determining the position of the surface feature 154 as shown, for example, in FIG. 6A, which is a close-up image of the map of surface features provided in FIG. 5, which, in turn, is a close-up image of the map of surface features provided in FIG. 4. The computer or equivalent device may subsequently use pixel interpolation for further mapping the surface feature 154 as shown in FIG. 6B.

Depending upon factors that may include the type of article, the type of surface features (e.g., particle, stain, scratch, void, etc.), and the like, it may be desirable at times to increase detection time of a single photon detector array or a plurality of photon detector arrays to detect more photons for detecting, mapping, and/or characterizing surface features of articles. In some embodiments, for example, detection time of a single photon detector array or a plurality of photon detector arrays may be increased to detect more fluoresced photons for detecting, mapping, and/or characterizing surface features of articles. In such embodiments, a CCD-based photon detector array, including an electron-multiplying EMCCD may be used to further detect more fluoresced photons for detecting, mapping, and/or characterizing surface features of articles. Alternately, or in addition, it may be desirable to increase the number of photons (e.g., photon energy) emitted from a single photon emitter or a plurality of photon emitters to provide an increase in photons scattered or photons fluoresced for detecting, mapping, and/or characterizing surface features of articles. Such an increase in photon energy may be with respect to unit time for increased photon power or photon flux, or with respect to unit area for increased photon flux density. Alternately to one or both of increasing the photon energy or detection time, or in addition to increasing the photon energy and detection time, it may be desirable at times to minimize background noise including stray light from one or more photon emitters, background light, and/or background fluorescent radiation.

The apparatus may further comprise one or more computers or equivalent devices (e.g., devices that include primary and/or secondary memory and one or more processing elements operable to carry out arithmetic and logical operations), including, but not limited to, servers, workstations, desktop computers, nettops, laptops, netbooks, and mobile devices such as tablets and smartphones, which computers or equivalent devices may contain application-specific integrated circuits ("ASIC"s), field-programmable gate arrays ("FPGA"s), etc. The computers or equivalent devices may include a computer-readable storage medium for instructions making the apparatus operable to, but not limited to, convey each article to the apparatus for inspection; position each article for inspection, optionally including gradational rotation of the article for piecewise inspection; hold or otherwise maintain the position of each article for inspection; insert optical components into the optical setup; position optical components for inspection; adjust optical components and/or tune optical components (e.g., piezoelectric-based wavelength filters; piezoelectric-based polarization filters; etc.) for inspection; remove optical components from the optical setup; move each photon emitter into position for inspection, wherein the position for inspection may include a photon emitter-article distance and/or angle (e.g., glancing angle) optimized for one or more types of features; switch each photon emitter on and off, or otherwise between modes for emitting photons and not emitting photons, including pulsing photons in accordance with a photon pulse-photon detection scheme; move each photon detector array into position for inspection, wherein the position for inspection may include a photon detector array-article distance and/or angle (e.g., scatter angle or emission angle) optimized for one or more types of features; switch each photon detector array on and off, or otherwise between modes for detecting photons and not detecting photons, including detecting photons in accordance with a photon pulse-photon detection scheme; synchronize each photon emitter with each photon detector in accordance with a photon pulse-photon detection scheme; process photon detector array signals from scattered photons or fluoresced photons, optionally including pixel interpolation for better accuracy (e.g., 10× better than pixel size) with respect to the position of surface features; map or otherwise determine the position of surface features of articles from photon detector array signals or processed photon detector array signals (e.g., photon scattering intensity distributions); quantitatively and/or qualitatively characterize surface features of articles, including classifying surface features as inorganic or organic; catalog surface features of articles; and determine trends with respect to surface features of articles.

Without being bound by theory, photons emitted by a photon emitter may be elastically or inelastically scattered from surface features of an article. With respect to elastic scattering (e.g., Rayleigh scattering), the energy (e.g., kinetic energy) of photons emitted by the photon emitter onto a surface of the article is conserved when such photons are scattered from surface features of the article. With respect to inelastic scattering (e.g., Raman scattering), the energy (e.g., kinetic energy) of photons emitted by the photon emitter onto the surface of the article is not conserved when such photons are scattered from surface features of the article, which may result in a red shift in the frequency of photons scattered from surface features of the article when compared to the frequency of photons emitted by the photon emitter onto the surface of the article. The red shift in the frequency of photons scattered from surface features of the article is indicative of energy lost to surface features of the article, which energy may be detected as fluorescence by a photon detector array in the absence of photons actively emitted by a photon emitter onto the surface of the article. Because the energy lost to surface features of the article is lost to organic surface features, organic surface features of an article may be detected by a photon detector array as fluorescence. Such fluorescence may be detected as photons are actively emitted onto the surface of the article using one or more combinations of photon emitters (e.g., monochromatic light-providing photon emitter), optical components (e.g., wavelength filter), and/or photon detectors described herein. Such fluorescence may be detected in the absence of photons actively emitted onto the surface of the article using one or more combinations of photon emitters, optical components, and/or photon detectors described herein.

In view of the foregoing, and with reference to FIG. 1 again, the photon detector array 130 (e.g., CMOS/sCMOS-based photon detector array) of the apparatus 100 may be configured to receive photons elastically and inelastically scattered from surface features of the article 150 for the surface features map 160A. FIG. 7A provides a close-up image of such a surface features map, which surface features map is for a surface of an article having inorganic and organic surface features. As evidenced by surface features map 160A of FIG. 7A, photons emitted by the photon emitter onto the surface of the article may be elastically scattered by inorganic surface features of the article and elastically or inelastically scattered by organic surface features of the article. With reference to FIG. 1 again, the same photon detector array 130 of the apparatus 100, or a different photon detector array (e.g., CCD-based photon detector array), may be configured to subsequently receive photons fluoresced from surface features of the article 150 for one or more additional surface features maps such as surface features maps 160B, 160C, and/or 160D of FIG. 7B. FIG. 7B provides close-up images of such surface features maps, which surface features maps are for the same surface of the article having inorganic and organic surface features; however, as evidenced by surface features map 160B, 160C, and 160D of FIG. 7B, photons emitted by a photon emitter onto the surface of the article may be inelastically scattered by organic surface features of the article resulting in fluorescence of the organic surface features, optionally in the absence of photons actively emitted by a photon emitter. The fluorescence intensity of such organic surface features decreases over time, which fluorescence intensity may be a function of organic species, size/volume of the organic surface features, or both organic species and size/volume of the organic surface features. Because the fluorescence intensity of such organic surface features may vary, compositing two or more surface features maps (e.g., 160B, 160C, 160D . . . 160n, wherein the index n indicates the $n^{th}$ surface features map) corresponding to photons fluoresced from surface features of the article 150 into one composite surface features map may be desirable at times (e.g., in the course of root cause failure analysis). Scatter-based surface features map 160A and fluorescence-based surface features map 160B, and/or any other fluorescence-based surface features maps (e.g., 160C, 160D . . . 160n, or a composite surface features map thereof), or the information sufficient to produce such surface features maps, may be used to characterize and/or differentiate surface features of articles. For example, scatter-based surface features map 160A and fluorescence-based surface features map 160B, and/or any other fluorescence-based surface features maps (e.g., 160C, 160D . . . 160n, or a composite surface features map thereof), or the information sufficient to produce such surface features maps, may be used to differentiate between inorganic and organic surface features of articles, as inorganic surface features exclusively show up in surface features map 160A.

FIG. 8 provides a schematic for detecting, mapping, and/or characterizing surface features of articles, illustrating an apparatus 100 comprising a primary photon emitter 110A (e.g., high-speed flash lamp), a secondary photon emitter 110B (e.g., laser), an optical setup 120, a photon detector array 130, and a computer or equivalent device 140, as well as an article 150 and a fluorescence decay analysis 165 for select organic surface features of an article 150, in accordance with an embodiment. As described in reference to FIG. 1, differential surface features maps 160A, 160B . . . 160n, wherein the index n indicates the $n^{th}$ surface features map 160n, or the information sufficient to produce such surface features maps, may be used to characterize surface features of articles and/or differentiate surface features of articles (e.g., differentiate between inorganic and organic surface features of articles); however, it may be desirable at times (e.g., in the course of root cause failure analysis) to further characterize surface features of articles and/or differentiate surface features of articles, especially when positional information for surface features of articles is known through a primary analysis (e.g., surface features map 160A). Further characterization of surface features of articles and/or differentiation of surface features of articles may include, for example, using the secondary photon emitter 110B (e.g., laser) to emit photons onto one or more (e.g., two or more, three or more, four or more, five or more, etc.) select organic surface features, thereby facilitating fluorescence of the one or more select organic surface features; detecting fluorescence of the one or more select organic surface features; and producing the fluorescence decay analysis 165 for the one or more select organic surface features of the article 150. Such a fluorescence decay analysis, or the information sufficient to produce the fluorescence decay analysis, may be used to further classify organic surface features by their chromophores and/or functional groups. Such a fluorescence decay analysis, or the information sufficient to produce the fluorescence decay analysis, may be also used to compare against one or more fluorescence decay analyses for a known organic surface features, or the information sufficient to produce the fluorescence decay analyses for the known organic surface features, for the purpose of identifying unknown organic surface features of articles.

FIG. 9 provides an example of a fluorescence decay analysis 165 for two select organic surface features, namely Organic A and Organic B, using a particular wavelength; however, such a fluorescence decay analysis may also be effected using different qualities of light (e.g., different wavelengths, polarization, coherence, and/or phase) described herein to extract additional comparative information for organic surface features with respect to their fluorescence decay. Producing the fluorescence decay analysis 165 for Organic A and Organic B includes, but is not limited to, using a laser as the secondary photon emitter 110B (see FIG. 8) to emit photons onto Organic A and Organic B, thereby facilitating fluorescence in Organic A and Organic B; detecting fluorescence of Organic A and Organic B; and plotting fluorescence intensity of Organic A and Organic B as a function of time. As evidenced by FIG. 9A, a photon emitter (e.g., laser) may be used to emit photons onto Organic A and Organic B in a sequence of pulses, and a photon detector array may be used to detect fluorescence of Organic A and Organic B, wherein each of the photon emitter and the photon detector array are synchronized in accordance with a photon pulse-photon detection scheme. The photon pulse-photon detection scheme used to produce the fluorescence decay analysis 165 of FIG. 9A includes, as shown, a first photon pulse of 0.6 seconds, followed by a first photon-pulse intermission of 1.4 seconds, followed by a second photon pulse of 0.6 seconds, followed by a second photon-pulse intermission of 1.4 seconds, etc., for a 0.6 second photon pulse starting every 2 seconds. The photon pulse-photon detection scheme used to produce the fluorescence decay analysis 165 of FIG. 9A further includes, as shown, continuous photon detection of photons fluoresced from Organic A and Organic B with respect to photon pulses. As such, the photon detector array may continuously detect photons fluoresced from Organic A and Organic B as the photon emitter actively emits photons onto the surface of the article and in the absence of the photon emitter actively emitting photons onto the surface of the article. To effect the continuous photon detection of photons fluoresced from Organic A and Organic B with respect to photon pulses, the photon detector array may be configured to detect photons fluoresced from Organic A and Organic B, for example, every 0.1 seconds.

Any combination of one or more photon emitters and one or more photon detector arrays described herein may be synchronized in a photon pulse-photon detection scheme for one or more surface features maps, one or more fluorescence decay analyses, or the information sufficient to produce the foregoing surface features maps or fluorescence decay analyses. FIG. 9B provides one such photon pulse-photon detection scheme for a synchronized combination of a photon emitter and a photon detector array. The photon pulse-photon detection scheme of FIG. 9B includes, as shown, a first photon pulse, followed by a first photon pulse-photon detection intermission ($\Delta t$), which, in turn, is followed by a first primary photon detection (e.g., for surface features map 160B of FIG. 7B) and a first secondary photon detection (e.g., for surface features map 160C of FIG. 7B), and so on, wherein $\Delta t$ is measured from the midpoint (in time) of a photon pulse and the midpoint (in time) of a subsequent photon detection. With respect to photon emitters, photon emitters may be configured to pulse photons at any photon-pulse frequency (e.g., photon pulses per unit time) and/or with any photon-pulse duration to effect characterization of surface features of articles. In some embodiments, for example, a photon emitter may be configured to pulse photons at least every 0.005, 0.01, 0.1, 0.2, 0.3, 0.4, 0.5, 0.6, 0.7, 0.8, or 0.9 seconds, or longer, such as at least every 1, 2, 3, 4, 5, 6, 7, 8, 9, or 10 seconds, optionally in tenths of a second thereof, in accordance with a photon pulse-photon detection scheme. In some embodiments, for example, a photon emitter may be configured to pulse photons in photon pulses having a duration of at least 0.1, 0.2, 0.3, 0.4, 0.5, 0.6, 0.7, 0.8, or 0.9 seconds, or longer, such as at least 1, 2, 3, 4, 5, 6, 7, 8, 9, or 10 seconds, optionally in tenths of a second thereof, in accordance with a photon pulse-photon detection scheme. With respect to photon detector arrays, photon detector arrays may be configured to detect photons at any photon-detection frequency (e.g., photon detections per unit time) and/or with any photon-detection duration (e.g., exposure time) to effect characterization of surface features of articles. In some embodiments, for example, a photon detector array may be configured to detect photons at least every 0.005, 0.01, 0.1, 0.2, 0.3, 0.4, 0.5, 0.6, 0.7, 0.8, or 0.9 seconds, or longer, such as at least every 1, 2, 3, 4, 5, 6, 7, 8, 9, or 10 seconds, optionally in tenths of a second thereof, in accordance with a photon pulse-photon detection scheme. In some embodiments, for example, a photon detector array may be configured to detect photons in exposure times of at least 0.1, 0.2, 0.3, 0.4, 0.5, 0.6, 0.7, 0.8, or 0.9 seconds, or longer, such as at least 1, 2, 3, 4, 5, 6, 7, 8, 9, or 10 seconds, optionally in tenths of a second thereof, in accordance with a photon pulse-photon detection scheme. Photon pulse-photon detection intermission values, which may be measured in seconds or tenths of seconds, may depend upon combinations of the foregoing photon-pulse frequencies, photon-pulse durations, photon-detection frequencies, and photon-detection durations (e.g., exposure times). The one or more computers or equivalent devices may be loaded with instructions making the apparatus operable to effect one or more of the foregoing possible photon pulse-photon detection schemes.

The apparatus may be operable to detect, map, and/or characterize surface features of articles that are nanometer-sized (i.e., admits of nm units as measured) or smaller in their smallest dimension (e.g., length, width, height, or depth, depending on the surface feature), which features may be smaller than the wavelength of photons emitted from a photon emitter of the apparatus. However, the apparatus is not limited to detecting, mapping, and/or characterizing surface features of articles that are nanometer-sized or smaller, as the apparatus may be operable to detect, map, and/or characterize surface features of articles that are micrometer-sized (i.e., admits of µm units as measured) or larger. In some embodiments, for example, the apparatus may be operable to detect, map, and/or characterize surface features of articles smaller than 500 nm, 250 nm, 200 nm, 150 nm, 125 nm, 110 nm, 100 nm, 90 nm, 80 nm, 70 nm, 60 nm, 50 nm, 40 nm, 30 nm, 20 nm, 10 nm, or 1 nm (10 Å) in their smallest dimension, or even smaller, such as surface features of articles smaller than 9 Å, 8 Å, 7 Å, 6 Å, 5 Å, 4 Å, 3 Å, 2 Å, or 1 Å in their smallest dimension. In view of the foregoing, the apparatus may be operable to, in some embodiments, for example, detect, map, and/or characterize surface features of articles between 0.1 nm and 1000 nm, such as between 0.1 nm and 500 nm, including between 0.1 nm and 250 nm, and further including between 0.1 nm and 100 nm, and even further including between 0.1 nm and 80 nm.

The apparatus may be operable to detect, map, and/or characterize certain features, including surface and/or subsurface defects comprising particle contamination in which the particles are nanometer-sized (i.e., admits of nm units as measured) or smaller in their smallest dimension (e.g., length, width, or height). In some embodiments, for example, the apparatus may be operable to detect, map, and/or characterize surface and/or subsurface particles smaller than 125 nm, such as smaller than 100 nm, including smaller than 80 nm, and further including smaller than 10 nm in their smallest dimension. Detecting, mapping, and/or characterizing surface and/or subsurface particles down to the level of 10 nm in height is important for hard disks of hard disk drives, as particles greater than 10 nm in height (e.g., from the surface) may corrupt the spacing between the hard disk and the read-write head of a hard disk drive. In some embodiments, for example, the apparatus may be operable to detect, map, and/or characterize surface and/or subsurface particles as small as or smaller than 4 nm in height.

The apparatus may be operable to detect, map, and/or characterize certain features, including surface and/or subsurface defects comprising scratches (e.g., circumferential scratches) that are micrometer-sized (i.e., admits of µm units as measured) or smaller, such as nanometer-sized (i.e., admits of nm units as measured) or smaller, such as angstrom-sized (i.e., admits of Å units as measured) or smaller, in their smallest dimension (e.g., length, width, or depth). With respect to micrometer-sized scratches, the apparatus may be operable to detect, map, and/or characterize scratches from, for example, 1 µm to 1000 µm in length, which may be significantly longer than the wavelength of photons emitted from a photon emitter of the apparatus. In some embodiments, for example, the apparatus may be operable to detect, map, and/or characterize surface features such as defects comprising scratches smaller than 1000 µm, such as smaller than 500 µm, including smaller than 250 µm, further including smaller than 100 µm, and even further including smaller than 50 µm in scratch length. With respect to nanometer-sized scratches, the apparatus may be operable to detect, map, and/or characterize scratches from, for example, 1 nm to 500 nm in scratch width. In some embodiments, for example, the apparatus may be operable to detect, map, and/or characterize surface features such as defects comprising scratches smaller than 500 nm, such as smaller than 250 nm, including smaller than 100 nm, further including smaller than 50 nm, and even further including smaller than 15 nm in scratch width. Surprisingly, due to a high level of spatial coherence, the apparatus may be operable to detect, map, and/or characterize angstrom-sized scratches with respect to scratch depth. In some embodiments, for example, the apparatus may be operable to detect, map, and/or characterize surface features such as defects comprising scratches smaller than 50 Å, such as smaller than 25 Å, including smaller than 10 Å, further including smaller than 5 Å, and even further including smaller than 1 Å (e.g., 0.5 Å) in scratch depth. For example, the apparatus may be operable to detect, map, and/or characterize surface features such as defects comprising scratches smaller than 500 μm in length, smaller than 100 nm in width, and smaller than 50 Å in depth.

The apparatus may be operable to accurately and/or precisely map or otherwise determine the position of a feature on an article's surface (e.g., FIGS. 6A (top) and 6B (top)). With respect to accuracy, the apparatus may be operable to map or otherwise determine the position of a feature on an article's surface within a micrometer-sized (i.e., admits of μm units as measured) radius or better. In some embodiments, for example, the apparatus may be operable to accurately map or otherwise determine the position of a feature on an article's surface within a radius of 100 μm, 90 μm, 80 μm, 70 μm, 60 μm, 50 μm, 40 μm, 30 μm, 20 μm, 10 μm, 9 μm, 8 μm, 7 μm, 6 μm, 5 μm, 4 μm, 3 μm, 2 μm, or 1 μm, or better. Combinations of the foregoing may also be used to describe the accuracy with which the apparatus may map or otherwise determine the position of a feature on an article's surface. In some embodiments, for example, the apparatus may be operable to accurately map or otherwise determine the position of a feature on an article's surface within a radius ranging from 1 μm to 100 μm, such as from 1 μm to 50 μm, including from 1 μm to 30 μm, and further including from 5 μm to 10 μm.

In addition to accurately and/or precisely mapping or otherwise determining the position of a feature on a surface of an article, the apparatus may be operable to accurately and/or precisely determine the photon scattering intensity distribution (e.g., FIGS. 6A (bottom) and 6B (bottom)) of the feature on the surface of the article. Such a photon scattering intensity distribution may be used characterize a surface feature of an article both quantitatively and qualitatively.

With respect to quantitative characterization of a surface feature of an article, mathematical integration of a photon scattering intensity distribution provides the size (e.g., volume) of the surface feature of the article. Quantitative characterization of a surface feature of an article may further include a determination of surface feature position on the article as described herein. Quantitative characterization may even further include the total number of surface features per article, or the number of surface features per unit area per article, as well as the number of each type of surface feature on the article. Such characterization information may be cataloged across a plurality of articles and be used to correct manufacturing trends should such features include surface and/or subsurface defects that might degrade the performance of the article.

With respect to qualitative characterization of a surface feature of an article, qualitative characterization may include a determination of the type of surface feature (e.g., particle, stain, scratch, void, etc.) of the article, which determination may be effected by, but is not limited to, analysis of photon scattering intensity distributions. Qualitative characterization may further include identifying surface features based upon one or more chemical signatures and/or distinguishing between surface features (e.g., inorganic vs. organic) based upon one or more chemical signatures, which distinguishing includes classifying such surface features based upon one or more chemical signatures, wherein chemical signatures include, but are not limited to, the manner by which photons are scattered (e.g., scatterometry) and/or the manner by which photons are fluoresced (or not fluoresced), including fluorescence intensity as a function of time. The foregoing chemical signatures may provide the information, part of the information, or otherwise be used for producing differential maps described herein, such as differential surface features maps 160A and 160B described in relation to FIG. 1. As such, in some embodiments, for example, qualitative characterization of one or more surface features of an article may comprise contrasting photon/light-scattering information with photon/light-fluorescing information or contrasting a first surface features map produced using photon/light-scattering information with a second surface features map (or a plurality of subsequent surface features maps) produced using photon/light-fluorescing information. Additionally, in some embodiments, for example, qualitative characterization of one or more surface features of an article may comprise analysis of fluorescence intensity as a function of time for the one or more surface features, including analysis of fluorescence intensity as a function of time for the one or more surface features against known surface features and the fluorescence intensity as a function of time for the known surface features. Along with quantitative characterization information, such qualitative characterization information may be cataloged across a plurality of articles and be used to correct manufacturing trends should such features include surface and/or subsurface defects that might degrade the performance of the article.

The apparatus described herein may be configured to process or inspect articles at a rate greater than or commensurate with the rate at which the articles or workpieces thereof are produced. In some embodiments, for example, the apparatus may be configured to process or inspect articles at a rate of at least 1, 2, 3, 4, 5, 6, 7, 8, 9, 10, 12, 14, 16, 18, or 20 article(s) per second, which rate may be commensurate with the rate at which the articles or workpieces thereof are produced. In some embodiments, for example, the apparatus may be configured to process or inspect articles at a rate of no more than 20, 18, 16, 14, 12, 10, 9, 8, 7, 6, 5, 4, 3, 2, or 1 article(s) per second, which rate may be commensurate with the rate at which the articles or workpieces thereof are produced. Combinations of the foregoing may also be used to describe the rate at which the articles or workpieces thereof are processed or inspected by the apparatus. In some embodiments, for example, the apparatus may be configured to process or inspect at least 1 and no more than 20 articles per second (e.g., between 1 and 20 articles per second), such as at least 1 and no more than 10 articles per second (e.g., between 1 and 10 articles per second), including at least 1 and no more than 5 articles per second (e.g., between 1 and 5 articles per second). Processing or inspecting articles at rates greater than or commensurate with the rate at which the articles or workpieces thereof are produced is a function of many features of the apparatus described herein, including, but not limited to, photon emitters and/or articles that need not be moved (e.g., for scanning) during processing or inspecting. For example, an article such as a hard disk of a hard disk drive need not be rotated during processing or inspecting. As such, the apparatus may be configured to hold an article stationary while emitting photons onto the surface of the article.

The apparatus described herein may be fully automated and function in different modes, including, but not limited to, an ultrafast mode, an ultrasensitive mode, and ultrasensitive plus mode. With respect to the ultrafast mode, the apparatus may operate at least 200 times faster than other optical surface analyzers (e.g., KLA-Tencor Candela CS10 or CS20), detect surface features such as defects comprising particles down to at least 100 nm, partially detect surface features such as defects comprising scratches (e.g., nanometer-sized scratches), and provide measurements of roughness. With respect to the ultrasensitive mode, the apparatus may operate at least 50 times faster than other optical surface analyzers, detect surface features such as defects comprising particles down to at least 30 nm, and provide measurements of roughness. With respect to the ultrasensitive plus mode, the apparatus may operate at least 20 times faster than other optical surface analyzers, detect surface features such as defects comprising particles down to at least 30 nm, fully detect surface features such as defects comprising scratches (e.g., nano-scratches), and provide measurements of roughness.

As such, provided herein is an apparatus, comprising a photon emitter configured to emit photons onto a surface of an article in a first photon pulse, a photon detector array configured to receive photons from surface features of the article; and a processing means configured for processing photon-detector-array signals corresponding to photons received by the photon detector array during the first photon pulse and subsequent to the first photon pulse, wherein the processing means is further configured for classifying the surface features of the article. In some embodiments, the apparatus further comprises a telecentric lens, wherein the telecentric lens is coupled to the photon detector array. In some embodiments, classifying the surface features comprises classifying the surface features as inorganic or organic by contrasting photon-detector-array signals corresponding to photons scattered from the surface features and photons fluoresced from the surface features. In some embodiments, the processing means is further configured for producing a map of the surface features from photons scattered from the surface features during the first photon pulse. In some embodiments, the processing means is further configured for producing one or more maps of the surface features from photons fluoresced from the surface features subsequent to the first photon pulse. In some embodiments, the map of the surface features from photons scattered from the surface features provides positional information for the surface features, and the one or more maps of the surface features from photons fluoresced from the surface features provides classifying information, optionally by contrast with the map of the surface features from photons scattered from the surface features. In some embodiments, the apparatus further comprises one or more additional photon emitters configured to emit photons onto the surface of the article. In some embodiments, the processing means is further configured for processing photon-detector-array signals corresponding to photons received by the photon detector array during one or more additional pulses of photons subsequent to the first photon pulse and in-between the one or more additional pulses of photons subsequent to the first photon pulse. In some embodiments, the processing means comprises one or more computers or equivalent devices, operable to classify the surface features from the photon-detector-array signals.

Also provided herein is an apparatus, comprising a photon emitter configured for emitting photons onto a surface of an article in a first photon pulse, a photon detector array coupled to a telecentric lens, configured for receiving photons from surface features of the article, wherein the photon emitter and the photon detector array are synchronized with respect to emitting photons and receiving photons; and a processing means configured for processing photon-detector-array signals corresponding to photons received by the photon detector array during one or more pulses of photons and in-between the one or more pulses of photons, wherein the processing means is further configured for classifying the surface features of the article. In some embodiments, classifying the surface features comprises classifying the surface features as inorganic or organic by contrasting photon-detector-array signals corresponding to photons scattered from the surface features and photons fluoresced from the surface features. In some embodiments, the processing means is further configured for producing one or more maps of the surface features from photons scattered from the surface features during the one or more pulses of photons. In some embodiments, the processing means is further configured for producing one or more maps of the surface features from photons fluoresced from the surface features in-between the one or more pulses of photons. In some embodiments, the processing means comprises one or more computers or equivalent devices operable to classify the surface features from the photon-detector-array signals.

Also provided herein is an apparatus, comprising a photon emitter configured to emit photons onto a surface of an article, a photon detector array configured to receive photons from surface features of the article; and a processing means configured for processing photon-detector-array signals corresponding to photons scattered from the surface features and photons fluoresced from the surface features, wherein the processing means is further configured for classifying the surface features of the article. In some embodiments, the apparatus further comprises a telecentric lens, wherein the telecentric lens is coupled to the photon detector array. In some embodiments, classifying the surface features comprises classifying the surface features as inorganic or organic by contrasting photon-detector-array signals corresponding to photons scattered from the surface features and photons fluoresced from the surface features. In some embodiments, the processing means is further configured for producing a map of the surface features from photons scattered from the surface features. In some embodiments, the processing means is further configured for producing a map of the surface features from photons fluoresced from the surface features. In some embodiments, the processing means comprises one or more computers or equivalent devices operable to classify the surface features from photon-detector-array signals.

While some particular embodiments have been described and/or illustrated herein, and while these particular embodiments have been described and/or illustrated in considerable detail, it is not the intention of the applicant(s) for these particular embodiments to limit the concepts presented herein. Additional adaptations and/or modifications may readily appear to persons having ordinary skill in the art, and, in broader aspects, these adaptations and/or modifications may be encompassed as well. Accordingly, departures may be made from the foregoing embodiments without departing from the scope of the concepts presented herein, which scope is limited only by the following claims when appropriately construed.

What is claimed is:
1. An apparatus, comprising:
a photon emitter configured to emit photons onto a surface of an article in a photon pulse;

a photon detector array coupled to a telecentric lens, configured to receive both scattered photons and fluoresced photons from surface features of the article, wherein the telecentric lens is a double telecentric lens; and a processing means configured for processing photon-detector-array signals corresponding to the scattered photons and the fluoresced photons received by the photon detector array during the photon pulse and subsequent to the photon pulse, respectively, and classifying the surface features from the photon-detector-array signals corresponding to the scattered photons and the fluoresced photons.

2. The apparatus of claim 1,
wherein classifying the surface features comprises classifying the surface features as inorganic or organic by contrasting the photon-detector-array signals corresponding to the scattered photons and the fluoresced photons.

3. The apparatus of claim 1,
wherein the processing means is further configured for producing
   a first map of the surface features from the scattered photons, and
   a second map of the surface features from the fluoresced photons.

4. The apparatus of claim 3,
wherein the first map provides positional information for the surface features, and
wherein the second map provides classifying information for the surface features by contrast with the first map.

5. The apparatus of claim 1,
wherein the processing means comprises one or more computers or equivalent devices operable to classify the surface features from the photon-detector-array signals.

6. An apparatus, comprising:
a photon emitter configured for emitting photons onto a surface of an article;
a photon detector array coupled to a telecentric lens, configured for receiving both scattered photons and fluoresced photons from surface features of the article, wherein
   the photon emitter and the photon detector array are synchronized with respect to emitting photons and receiving photons, and
   the photon emitter is a flash lamp configured to minimize vibrations while the photon detector array receives the scattered photons; and
a processing means configured for
   processing photon-detector-array signals corresponding to the scattered photons and the fluoresced photons received by the photon detector array during one or more pulses of photons and in-between the one or more pulses of photons, respectively, and
   classifying the surface features from the photon-detector-array signals corresponding to the scattered photons and the fluoresced photons.

7. The apparatus of claim 6,
wherein classifying the surface features comprises classifying the surface features as inorganic or organic by contrasting the photon-detector-array signals corresponding to the scattered photons and the fluoresced photons.

8. The apparatus of claim 6,
wherein the processing means is further configured for producing one or more image maps of the surface features from the scattered photons during the one or more pulses of photons.

9. The apparatus of claim 8,
wherein the processing means is further configured for producing one or more image maps of the surface features from the fluoresced photons in-between the one or more pulses of photons.

10. The apparatus of claim 6,
wherein the processing means comprises one or more computers or equivalent devices operable to classify the surface features by contrasting one or more image maps of the surface features derived from the scattered photons with one or more image maps of the surface features derived from the fluoresced photons.

11. An apparatus, comprising:
a photon detector array coupled to a telecentric lens, configured to receive both scattered photons and fluoresced photons from surface features of an article, wherein the telecentric lens is a double telecentric lens; and
a processing means configured for
   processing photon-detector-array signals corresponding to the scattered photons and the fluoresced photons received by the photon detector array during one or more pulses of photons and in-between the one or more pulses of photons, respectively, and
   classifying the surface features from the photon-detector-array signals corresponding to the scattered photons and the fluoresced photons.

12. The apparatus of claim 11,
wherein classifying the surface features comprises classifying the surface features as inorganic or organic by contrasting the photon-detector-array signals corresponding to the scattered photons and the fluoresced photons.

13. The apparatus of claim 11,
wherein the processing means is further configured for
   producing a first image map of the surface features from the scattered photons and a second image map of the surface features from the fluoresced photons, and
   classifying the surface features as inorganic or organic by contrasting the first image map and the second image map.

14. The apparatus of claim 11,
wherein the processing means comprises one or more computers or equivalent devices operable to classify the surface features from the photon-detector-array signals.

15. The apparatus of claim 1,
wherein the photon detector array is a sCMOS-based photon detector array configured for imaging.

16. The apparatus of claim 1,
wherein the apparatus is configured to hold the article in a stationary position without rotation while the photon detector array receives the scattered photons and the fluoresced photons.

17. The apparatus of claim 16,
wherein the photon emitter is a flash lamp configured to minimize vibrations while the photon detector array receives the scattered photons.

18. The apparatus of claim 17, further comprising:
an additional photon emitter for fluorescence decay analysis of organic surface features, wherein the additional photon emitter is a laser.

19. The apparatus of claim 7,
wherein the processing means is further configured for determining sizes of the surface features by analyzing scattering intensity distributions associated with the first map.

\* \* \* \* \*

UNITED STATES PATENT AND TRADEMARK OFFICE
CERTIFICATE OF CORRECTION

PATENT NO. : 9,297,759 B2
APPLICATION NO. : 14/032187
DATED : March 29, 2016
INVENTOR(S) : Joachim Walter Ahner et al.

It is certified that error appears in the above-identified patent and that said Letters Patent is hereby corrected as shown below:

Claims

In Column 23 line 1, claim 19, delete "7" and insert --4--, therefore.

Signed and Sealed this
Twenty-eighth Day of June, 2016

Michelle K. Lee
*Director of the United States Patent and Trademark Office*